United States Patent
Messerly et al.

(10) Patent No.: US 11,065,048 B2
(45) Date of Patent: Jul. 20, 2021

(54) FLEXIBLE CIRCUIT ARRANGEMENT FOR SURGICAL FASTENING INSTRUMENTS

(71) Applicant: Ethicon LLC, Guaynabo, PR (US)

(72) Inventors: Jeffrey D. Messerly, Cincinnati, OH (US); David C. Yates, West Chester, OH (US); Jason L. Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 754 days.

(21) Appl. No.: 15/636,123

(22) Filed: Jun. 28, 2017

(65) Prior Publication Data
US 2019/0000531 A1 Jan. 3, 2019

(51) Int. Cl.
*A61B 18/14* (2006.01)
*A61B 17/072* (2006.01)
(Continued)

(52) U.S. Cl.
CPC .... *A61B 18/1442* (2013.01); *A61B 17/07207* (2013.01); *A61B 17/29* (2013.01); *A61B 17/3205* (2013.01); *A61B 18/1445* (2013.01); *A61B 17/295* (2013.01); *A61B 2017/00026* (2013.01); *A61B 2017/0046* (2013.01);
(Continued)

(58) Field of Classification Search
CPC ... A61B 17/068; A61B 17/285; A61B 17/295; A61B 2017/07285; A61B 2017/2905; A61B 2017/2908; A61B 2017/2932; A61B 2017/2937; A61B 2017/18; A61B 2017/1442; A61B 2018/1452; A61B 2018/1455; A61B 34/30; A61B 2034/305
See application file for complete search history.

(56) References Cited

U.S. PATENT DOCUMENTS 2,961,385 A 11/1960 McGall
3,370,263 A 2/1968 Schreieck
(Continued)

FOREIGN PATENT DOCUMENTS

| GB | 1526401 A | 9/1978 |
|---|---|---|
| JP | 2004130126 A | 4/2004 |
| WO | WO-9937225 A1 | 7/1999 |

OTHER PUBLICATIONS

Bay Area Circuits (https://bayareacircuits.com/multi-layer-stackups/) (Year: 2015).

*Primary Examiner* — Ronald Hupczey, Jr.

(57) ABSTRACT

A flexible assembly of a motor driven surgical system may include a flexible shaft circuit strip and a knife bar having a first laminated plate disposed along a first side of the circuit strip and a second laminated plate disposed along a second side of the circuit strip. The knife bar may reciprocate along a longitudinal axis of the circuit strip. Each laminated plate may be composed of a pair of laminated plates. The flexible assembly may include a first leaf spring disposed between the first side of the circuit strip and the first laminated plate, and a second leaf spring disposed between the second side of the circuit strip and the second laminated plate. The flexible assembly may be disposed within at least a portion of a distal portion of an articulating shaft and at least a portion of an articulation connector of the surgical device.

19 Claims, 22 Drawing Sheets

(51) Int. Cl.
*A61B 17/29* (2006.01)
*A61B 17/3205* (2006.01)
*A61B 17/00* (2006.01)
*A61B 18/00* (2006.01)
*A61B 90/00* (2016.01)
*A61B 17/295* (2006.01)

(52) U.S. Cl.
CPC .............. *A61B 2017/00075* (2013.01); *A61B 2017/00119* (2013.01); *A61B 2017/00128* (2013.01); *A61B 2017/00353* (2013.01); *A61B 2017/00398* (2013.01); *A61B 2017/00477* (2013.01); *A61B 2017/00734* (2013.01); *A61B 2017/07271* (2013.01); *A61B 2017/07285* (2013.01); *A61B 2017/2902* (2013.01); *A61B 2017/2927* (2013.01); *A61B 2018/00184* (2013.01); *A61B 2018/00589* (2013.01); *A61B 2018/00916* (2013.01); *A61B 2018/1455* (2013.01); *A61B 2090/061* (2016.02); *A61B 2090/065* (2016.02)

(56) References Cited

U.S. PATENT DOCUMENTS

| | | | |
|---|---|---|---|
| D278,081 | S | 3/1985 | Green |
| D297,764 | S | 9/1988 | Hunt et al. |
| 5,007,907 | A | 4/1991 | Nishigaki et al. |
| 5,364,395 | A | 11/1994 | West, Jr. |
| 5,403,312 | A | 4/1995 | Yates et al. |
| D360,688 | S | 7/1995 | Ferragamo et al. |
| 5,485,947 | A | 1/1996 | Olson et al. |
| 5,658,281 | A | 8/1997 | Heard |
| 5,673,842 | A | 10/1997 | Bittner et al. |
| 5,735,848 | A | 4/1998 | Yates et al. |
| 5,817,093 | A | 10/1998 | Williamson, IV et al. |
| 5,827,279 | A | 10/1998 | Hughett et al. |
| 5,833,690 | A | 11/1998 | Yates et al. |
| 5,835,829 | A | 11/1998 | Genovese et al. |
| 6,004,320 | A | 12/1999 | Casscells et al. |
| D480,808 | S | 10/2003 | Wells et al. |
| 6,730,081 | B1 | 5/2004 | Desai |
| 6,905,497 | B2 | 6/2005 | Truckai et al. |
| 6,918,906 | B2 | 7/2005 | Long |
| D509,297 | S | 9/2005 | Wells |
| 6,988,649 | B2 | 1/2006 | Shelton, IV et al. |
| 7,044,352 | B2 | 5/2006 | Shelton, IV et al. |
| 7,223,267 | B2 | 5/2007 | Isola et al. |
| 7,383,611 | B2 | 6/2008 | Foster |
| D576,278 | S | 9/2008 | Nalagatla et al. |
| 7,431,720 | B2 | 10/2008 | Pendekanti et al. |
| 7,476,222 | B2 | 1/2009 | Sun et al. |
| 7,517,356 | B2 | 4/2009 | Heinrich |
| 7,559,452 | B2 | 7/2009 | Wales et al. |
| 7,575,144 | B2 | 8/2009 | Ortiz et al. |
| 7,617,961 | B2 | 11/2009 | Viola |
| D605,762 | S | 12/2009 | Nalagatla et al. |
| 7,673,781 | B2 | 3/2010 | Swayze et al. |
| 7,780,663 | B2 | 8/2010 | Yates et al. |
| 7,819,296 | B2 | 10/2010 | Hueil et al. |
| 7,861,906 | B2 | 1/2011 | Doll et al. |
| 7,896,877 | B2 | 3/2011 | Hall et al. |
| 7,901,400 | B2 | 3/2011 | Wham et al. |
| D650,074 | S | 12/2011 | Hunt et al. |
| 8,277,446 | B2 | 10/2012 | Heard |
| 8,453,906 | B2 | 6/2013 | Huang et al. |
| 8,465,534 | B2 | 6/2013 | Schechter |
| 8,485,413 | B2 | 7/2013 | Scheib et al. |
| 8,517,239 | B2 | 8/2013 | Scheib et al. |
| 8,523,043 | B2 | 9/2013 | Ullrich et al. |
| 8,579,176 | B2 | 11/2013 | Smith et al. |
| 8,608,045 | B2 | 12/2013 | Smith et al. |
| 8,616,431 | B2 | 12/2013 | Timm et al. |
| 8,622,274 | B2 | 1/2014 | Yates et al. |
| 8,636,736 | B2 | 1/2014 | Yates et al. |
| 8,663,222 | B2 | 3/2014 | Anderson et al. |
| 8,708,213 | B2 | 4/2014 | Shelton, IV et al. |
| 8,746,533 | B2 | 6/2014 | Whitman et al. |
| 8,764,747 | B2 | 7/2014 | Cummings et al. |
| 8,784,415 | B2 | 7/2014 | Malackowski et al. |
| 8,820,603 | B2 | 9/2014 | Shelton, IV et al. |
| 8,840,603 | B2 | 9/2014 | Shelton, IV et al. |
| 8,858,547 | B2 | 10/2014 | Brogna |
| 8,876,858 | B2 | 11/2014 | Braun |
| 8,888,771 | B2 | 11/2014 | Twomey |
| 8,888,776 | B2 | 11/2014 | Dietz et al. |
| 8,926,607 | B2 | 1/2015 | Norvell et al. |
| 8,968,317 | B2 | 3/2015 | Evans et al. |
| 8,979,890 | B2 | 3/2015 | Boudreaux |
| 8,998,060 | B2 | 4/2015 | Bruewer et al. |
| 9,005,199 | B2 | 4/2015 | Beckman et al. |
| 9,060,775 | B2 | 6/2015 | Wiener et al. |
| 9,060,776 | B2 | 6/2015 | Yates et al. |
| 9,072,535 | B2 | 7/2015 | Shelton, IV et al. |
| 9,149,325 | B2 | 10/2015 | Worrell et al. |
| 9,161,802 | B2 | 10/2015 | Przybyszewski |
| 9,326,788 | B2 | 5/2016 | Batross et al. |
| 9,345,481 | B2 | 5/2016 | Hall et al. |
| 9,358,003 | B2 | 6/2016 | Hall et al. |
| 9,402,627 | B2 | 8/2016 | Stevenson et al. |
| 9,510,906 | B2 | 12/2016 | Boudreaux et al. |
| 9,526,564 | B2 | 12/2016 | Rusin |
| 9,549,733 | B2 | 1/2017 | Knodel |
| 9,561,031 | B2 | 2/2017 | Heinrich et al. |
| 9,566,062 | B2 | 2/2017 | Boudreaux |
| 9,572,622 | B2 | 2/2017 | Shelton, IV et al. |
| 9,585,657 | B2 | 3/2017 | Shelton, IV et al. |
| 9,629,627 | B2 | 4/2017 | Kostrzewski et al. |
| 9,629,628 | B2 | 4/2017 | Aranyi |
| 9,700,309 | B2 | 7/2017 | Jaworek et al. |
| 9,706,993 | B2 | 7/2017 | Hessler et al. |
| 9,707,028 | B2 | 7/2017 | Batchelor et al. |
| 9,724,095 | B2 | 8/2017 | Gupta et al. |
| 9,743,929 | B2 | 8/2017 | Leimbach et al. |
| 9,757,142 | B2 | 9/2017 | Shimizu |
| D800,904 | S | 10/2017 | Leimbach et al. |
| 9,788,835 | B2 | 10/2017 | Morgan et al. |
| 9,788,836 | B2 | 10/2017 | Overmyer et al. |
| 9,795,379 | B2 | 10/2017 | Leimbach et al. |
| 9,808,246 | B2 | 11/2017 | Shelton, IV et al. |
| 9,814,514 | B2 | 11/2017 | Shelton, IV et al. |
| 9,839,421 | B2 | 12/2017 | Zerkle et al. |
| 9,844,375 | B2 | 12/2017 | Overmyer et al. |
| 9,877,722 | B2 | 1/2018 | Schellin et al. |
| D809,659 | S | 2/2018 | Menn |
| 9,888,958 | B2 | 2/2018 | Evans et al. |
| 9,913,642 | B2 | 3/2018 | Leimbach et al. |
| 9,924,942 | B2 | 3/2018 | Swayze et al. |
| 9,924,944 | B2 | 3/2018 | Shelton, IV et al. |
| 9,924,998 | B2 | 3/2018 | Martin et al. |
| 9,968,355 | B2 | 5/2018 | Shelton, IV et al. |
| 9,980,769 | B2 | 5/2018 | Trees et al. |
| 10,010,366 | B2 | 7/2018 | Strobl |
| 10,016,186 | B2 | 7/2018 | Benn |
| 10,052,100 | B2 | 8/2018 | Morgan et al. |
| D831,209 | S | 10/2018 | Huitema et al. |
| D836,198 | S | 12/2018 | Harris et al. |
| 10,178,992 | B2 | 1/2019 | Wise et al. |
| 10,194,912 | B2 | 2/2019 | Scheib et al. |
| 10,201,348 | B2 | 2/2019 | Scheib et al. |
| 10,211,586 | B2 | 2/2019 | Adams et al. |
| 10,213,198 | B2 | 2/2019 | Aronhalt et al. |
| 10,231,776 | B2 | 3/2019 | Artale et al. |
| 10,238,385 | B2 | 3/2019 | Yates et al. |
| 10,245,027 | B2 | 4/2019 | Shelton, IV et al. |
| 10,265,120 | B2 | 4/2019 | Yates et al. |
| D847,989 | S | 5/2019 | Shelton, IV et al. |
| D850,617 | S | 6/2019 | Shelton, IV et al. |
| 10,327,776 | B2 | 6/2019 | Harris et al. |
| 10,335,147 | B2 | 7/2019 | Rector et al. |
| 10,357,305 | B2 | 7/2019 | Esch et al. |
| 10,413,291 | B2 | 9/2019 | Worthington et al. |
| D865,175 | S | 10/2019 | Widenhouse et al. |

(56) References Cited

U.S. PATENT DOCUMENTS

| | | |
|---|---|---|
| 10,456,137 B2 | 10/2019 | Vendely et al. |
| 10,470,768 B2 | 11/2019 | Harris et al. |
| 10,485,567 B2 | 11/2019 | Piskun |
| 10,548,504 B2 | 2/2020 | Shelton, IV et al. |
| 10,617,412 B2 | 4/2020 | Shelton, IV et al. |
| D893,717 S | 8/2020 | Messerly et al. |
| D908,216 S | 1/2021 | Messerly et al. |
| 2004/0122423 A1 | 6/2004 | Dycus et al. |
| 2006/0064086 A1 | 3/2006 | Odom |
| 2008/0147062 A1 | 6/2008 | Truckai et al. |
| 2009/0206133 A1 | 8/2009 | Morgan et al. |
| 2010/0193566 A1 | 8/2010 | Scheib et al. |
| 2010/0193567 A1* | 8/2010 | Scheib .............. A61B 17/07207 227/176.1 |
| 2011/0028964 A1 | 2/2011 | Edwards |
| 2011/0106076 A1 | 5/2011 | Hernandez Zendejas |
| 2011/0125176 A1 | 5/2011 | Yates et al. |
| 2012/0016413 A1 | 1/2012 | Timm et al. |
| 2012/0245576 A1 | 9/2012 | Epstein et al. |
| 2014/0263541 A1 | 9/2014 | Leimbach et al. |
| 2014/0263552 A1 | 9/2014 | Hall et al. |
| 2015/0060519 A1 | 3/2015 | Shelton, IV et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2016/0066913 A1 | 3/2016 | Swayze et al. |
| 2016/0120545 A1 | 5/2016 | Shelton, IV et al. |
| 2016/0270842 A1 | 9/2016 | Strobl et al. |
| 2017/0105782 A1 | 4/2017 | Scheib et al. |
| 2017/0105786 A1 | 4/2017 | Scheib et al. |
| 2017/0119388 A1 | 5/2017 | Kostrzewski |
| 2017/0143336 A1 | 5/2017 | Shah et al. |
| 2017/0296213 A1 | 10/2017 | Swensgard et al. |
| 2017/0312019 A1 | 11/2017 | Trees et al. |
| 2018/0168621 A1 | 6/2018 | Shelton, IV et al. |
| 2018/0168650 A1 | 6/2018 | Shelton, IV et al. |
| 2018/0360452 A1 | 12/2018 | Shelton, IV et al. |
| 2019/0000463 A1 | 1/2019 | Shelton, IV et al. |
| 2019/0000464 A1 | 1/2019 | Shelton, IV et al. |
| 2019/0000468 A1 | 1/2019 | Adams et al. |
| 2019/0000470 A1 | 1/2019 | Yates et al. |
| 2019/0000472 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000532 A1 | 1/2019 | Shelton, IV et al. |
| 2019/0000533 A1 | 1/2019 | Messerly et al. |
| 2019/0000534 A1 | 1/2019 | Messerly et al. |
| 2019/0000535 A1 | 1/2019 | Messerly et al. |
| 2019/0000537 A1 | 1/2019 | Widenhouse et al. |
| 2019/0000538 A1 | 1/2019 | Widenhouse et al. |
| 2019/0000539 A1 | 1/2019 | Messerly et al. |
| 2019/0000555 A1 | 1/2019 | Schings et al. |
| 2020/0397432 A1 | 12/2020 | Messerly et al. |

* cited by examiner

FLEXIBLE CIRCUIT ARRANGEMENT FOR SURGICAL FASTENING INSTRUMENTS

TECHNICAL FIELD

The present disclosure relates to electrosurgical devices and, in various aspects, to circuit components that are designed to conduct electrical signals between a proximal end and a distal end thereof.

BACKGROUND

In some aspects, an electrosurgical device may have an articulating shaft to permit a user to adjust an angle of an end effector with respect to a handle assembly in order to access tissues at any orientation with respect to the user. Electrical signals exchanged between the end effector and the handle assembly should be unimpeded regardless of the type or extent of the articulation of the shaft.

SUMMARY

In one aspect, a motor driven surgical system may include a handle assembly and an interchangeable surgical tool assembly, operatively coupled to the handle assembly. An aspect of the interchangeable surgical tool assembly may include a nozzle assembly, a proximal closure tube having a proximal end operatively coupled to a distal end of the nozzle assembly, an articulation connector having a proximal end operatively coupled to a distal end of the proximal closure tube, a surgical end effector including a first jaw and a second jaw and having a proximal end operatively coupled to a distal end of the articulation connector, a flexible shaft circuit strip disposed within at least a portion of the proximal closure tube, at least a portion of the articulation connector, and at least a portion of the surgical end effector, a knife member slideably disposed within the surgical end effector, and a knife bar operatively connected to a proximal end of the knife member. The knife bar may further include a first laminated plate disposed on a first side of the flexible shaft circuit strip and a second laminated plate disposed on a second side of the flexible shaft circuit strip, and the knife bar may be configured to reciprocate along a longitudinal axis of the proximal closure tube.

An aspect of a flexible assembly for use within an articulated component of a motor driven surgical system may include a flexible shaft circuit strip and a knife bar having a first laminated plate disposed along a first side of the flexible shaft circuit strip and a second laminated plate disposed along a second side of the flexible shaft circuit strip, in which the knife bar is configured to reciprocate along a longitudinal axis of the flexible shaft circuit strip.

FIGURES

The novel features of the aspects described herein are set forth with particularity in the appended claims. These aspects, however, both as to organization and methods of operation may be better understood by reference to the following description, taken in conjunction with the accompanying drawings.

DESCRIPTION

Figure 1:
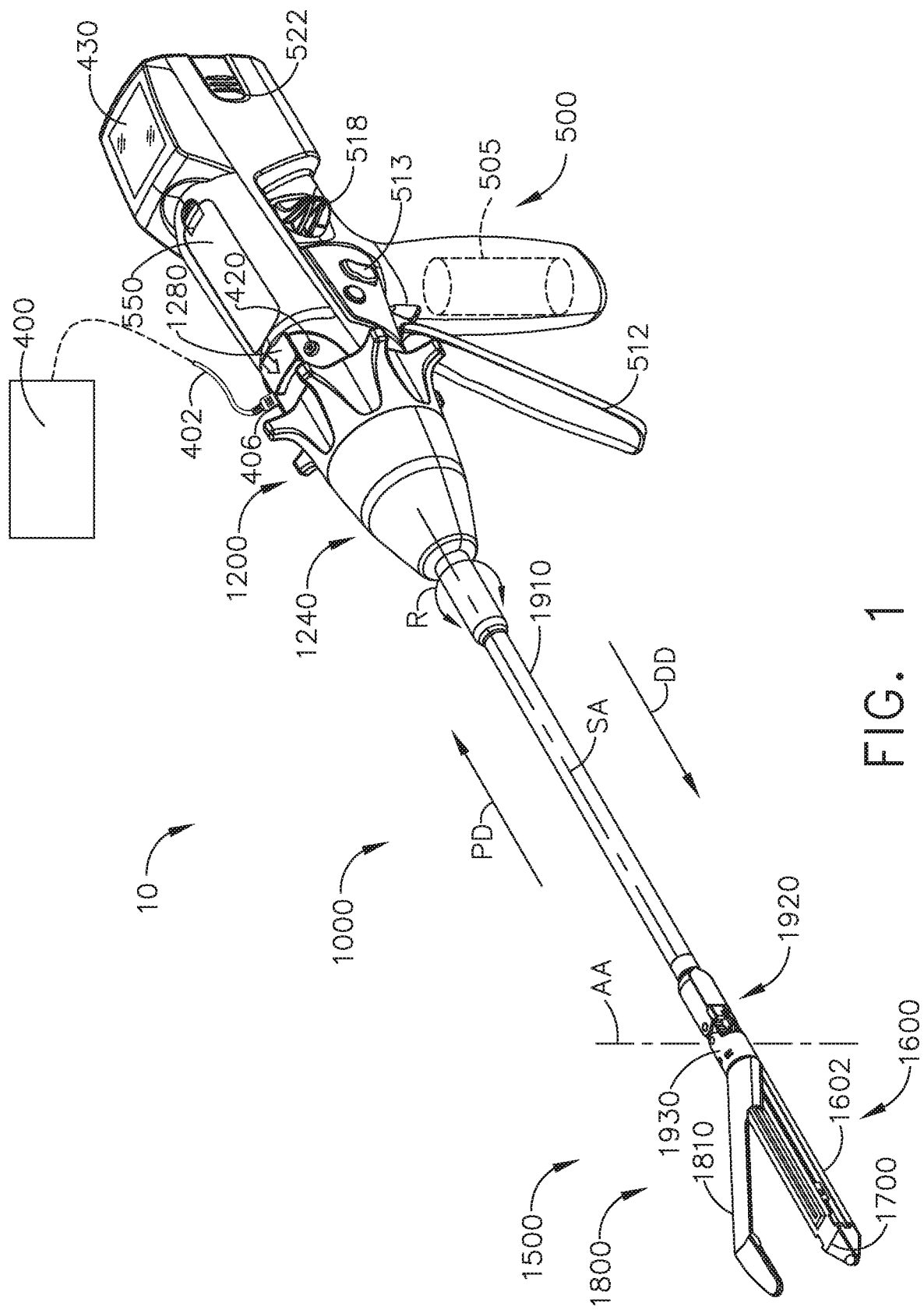
FIG. 1 is a perspective view of a surgical system including a handle assembly coupled to an interchangeable surgical tool assembly that is configured to be used in connection with conventional surgical staple/fastener cartridges and radio frequency (RF) cartridges according to one aspect of this disclosure.

Applicant of the present application owns the following patent applications filed Jun. 28, 2017 and which are each herein incorporated by reference in their respective entireties:

U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, by inventors Jeffrey D. Messerly et al., filed Jun. 28, 2017, now U.S. Patent Application Publication No. 2019/0000478.

U.S. patent application Ser. No. 15/636,103, titled SYSTEMS AND METHODS OF DISPLAYING SURGICAL INSTRUMENT STATUS, by inventors Jeffrey D. Messerly et al., filed Jun. 28, 2017, now U.S. Patent Application Publication No. 2019/0000533.

U.S. patent application Ser. No. 15/636,110, titled SHAFT MODULE CIRCUITRY ARRANGEMENTS, by inventors Jeffrey D. Messerly et al., filed Jun. 28, 2017, now U.S. Patent Application Publication No. 2019/0000525.

U.S. patent application Ser. No. 15/636,116, titled SYSTEMS AND METHODS FOR CONTROLLING CONTROL CIRCUITS FOR INDEPENDENT ENERGY DELIVERY OVER SEGMENTED SECTIONS, by inventors Jeffrey D. Messerly et al., filed Jun. 28, 2017, now U.S. Patent Application Publication No. 2019/0000534.

U.S. patent application Ser. No. 15/636,134, titled SURGICAL SYSTEM COUPLEABLE WITH STAPLE CARTRIDGE AND RADIO FREQUENCY CARTRIDGE, AND HAVING A PLURALITY OF RADIO-FREQUENCY ENERGY RETURN PATHS, by inventors Jeffrey D. Messerly et al., filed Jun. 28, 2017, now U.S. Patent Application Publication No. 2019/0000535.

U.S. patent application Ser. No. 15/636,144, titled SYSTEMS AND METHODS FOR CONTROLLING CONTROL CIRCUITS FOR AN INDEPENDENT ENERGY DELIVERY OVER SEGMENTED SECTIONS, by inventors David C. Yates et al., filed Jun. 28, 2017, now U.S. Pat. No. 10,265,120.

U.S. patent application Ser. No. 15/636,150, titled SURGICAL END EFFECTOR FOR APPLYING ELECTROSURGICAL ENERGY TO DIFFERENT ELECTRODES ON DIFFERENT TIME PERIODS, by inventors Tamara Widenhouse et al., filed Jun. 28, 2017, now U.S. Patent Application Publication No. 2019/0000537.

U.S. patent application Ser. No. 15/636,162, titled ELECTROSURGICAL CARTRIDGE FOR USE IN THIN PROFILE SURGICAL CUTTING AND STAPLING INSTRUMENT, by inventors Tamara Widenhouse et al., filed Jun. 28, 2017, now U.S. Patent Application Publication No. 2019/0000538.

U.S. patent application Ser. No. 15/636,169, titled SURGICAL END EFFECTOR TO ADJUST JAW COMPRESSION, by inventors Frederick E. Shelton, IV et al., filed Jun. 28, 2017, now U.S. Patent Application Publication No. 2019/0000532.

U.S. patent application Ser. No. 15/636,177, titled CARTRIDGE ARRANGEMENTS FOR SURGICAL CUTTING AND FASTENING INSTRUMENTS WITH LOCKOUT DISABLEMENT FEATURES, by inventors Jason L. Harris et al., filed Jun. 28, 2017, now U.S. Patent Application Publication No. 2019/0000479.

U.S. patent application Ser. No. 15/636,180, titled SURGICAL CUTTING AND FASTENING INSTRUMENTS WITH DUAL POWER SOURCES, by inventors Jeffrey D. Messerly et al., filed Jun. 28, 2017, now U.S. Patent Application Publication No. 2019/0000539.

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaw members. At least one of the jaw members may have at least one electrode. At least one jaw may be moveable from a position spaced apart from the opposing jaw for receiving tissues to a position in which the space between the jaw members is less than that of the first position. This movement of the moveable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example. The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by electrosurgical devices can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Figure 2:
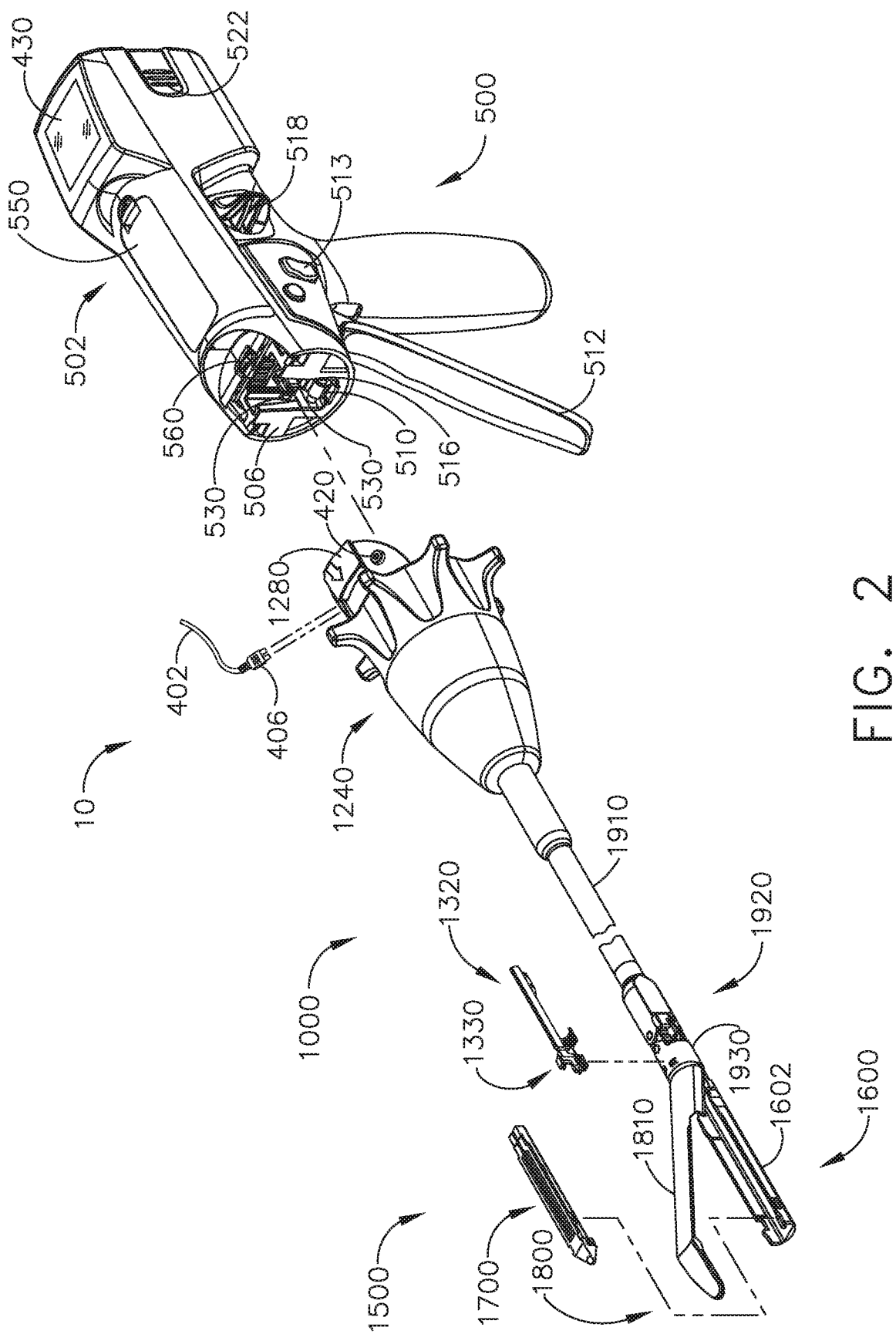
FIG. 2 is an exploded perspective assembly view of the surgical system of FIG. 1 according to one aspect of this disclosure.

FIGS. 1 and 2 depict a motor-driven surgical system 10 that may be used to perform a variety of different surgical procedures. In the illustrated arrangement, the surgical system 10 comprises an interchangeable surgical tool assembly 1000 that is operably coupled to a handle assembly 500. In another surgical system aspect, the interchangeable surgical tool assembly 1000 may also be effectively employed with a tool drive assembly of a robotically controlled or automated surgical system. For example, the surgical tool assembly 1000 disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

In the illustrated aspect, the handle assembly 500 may comprise a handle housing 502 that includes a pistol grip portion 504 that can be gripped and manipulated by the clinician. As will be briefly discussed below, the handle assembly 500 operably supports a plurality of drive systems that are configured to generate and apply various control motions to corresponding portions of the interchangeable surgical tool assembly 1000. As shown in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microcontroller in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries may be connected in series may be used as the power source 522 for the surgical system 10. In addition, the power source 522 may be replaceable and/or rechargeable.

The electric motor 505 is configured to axially drive a longitudinally movable drive member 540 (FIG. 3) in a distal and proximal directions depending upon the polarity of the motor. For example, when the motor 505 is driven in one rotary direction, the longitudinally movable drive member will be axially driven in a distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger (not shown) that is adjacent to the closure trigger 512 and pivotally supported on the handle assembly 500. The firing trigger may be pivoted between an unactuated position and an actuated position. The firing trigger may be biased into the unactuated position by a spring or other biasing arrangement such that when the clinician releases the firing trigger, it may be pivoted or otherwise returned to the unactuated position by the spring or biasing arrangement. In at least one form, the firing trigger can be positioned "outboard" of the closure trigger 512. As discussed in U.S. Patent Application Publication No. 2015/0272575, the handle assembly 500 may be equipped with a firing trigger safety button (not shown) to prevent inadvertent actuation of the firing trigger. When the closure trigger 512 is in the unactuated position, the safety button is contained in the handle assembly 500 where the clinician cannot readily access it and move it between a safety position preventing actuation of the firing trigger and a firing position wherein the firing trigger may be fired. As the clinician depresses the closure trigger, the safety button and the firing trigger pivot down wherein they can then be manipulated by the clinician.

In at least one form, the longitudinally movable drive member 540 may have a rack of teeth 542 formed thereon for meshing engagement with a corresponding drive gear arrangement (not shown) that interfaces with the motor. See FIG. 3. Further details regarding those features may be found in U.S. Patent Application Publication No. 2015/0272575. In at least one arrangement, however, the longitudinally movable drive member is insulated to protect it from inadvertent RF energy. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member 540 by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

In the illustrated aspect, the interchangeable surgical tool assembly 1000 includes a surgical end effector 1500 that comprises a first jaw 1600 and a second jaw 1800. In one arrangement, the first jaw comprises an elongate channel 1602 that is configured to operably support a conventional (mechanical) surgical staple/fastener cartridge 1400 (FIG. 4) or a radio frequency (RF) cartridge 1700 (FIGS. 1 and 2) therein. The second jaw 1800 comprises an anvil 1810 that is pivotally supported relative to the elongate channel 1602. The anvil 1810 may be is selectively moved toward and away from a surgical cartridge supported in the elongate channel 1602 between open and closed positions by actuating the closure drive system 510. In the illustrated arrangement, the anvil 1810 is pivotally supported on a proximal end portion of the elongate channel 1602 for selective pivotal travel about a pivot axis that is transverse to the shaft axis SA. Actuation of the closure drive system 510 may result in the distal axial movement of a proximal closure member or proximal closure tube 1910 that is attached to an articulation connector 1920.

Figure 3:
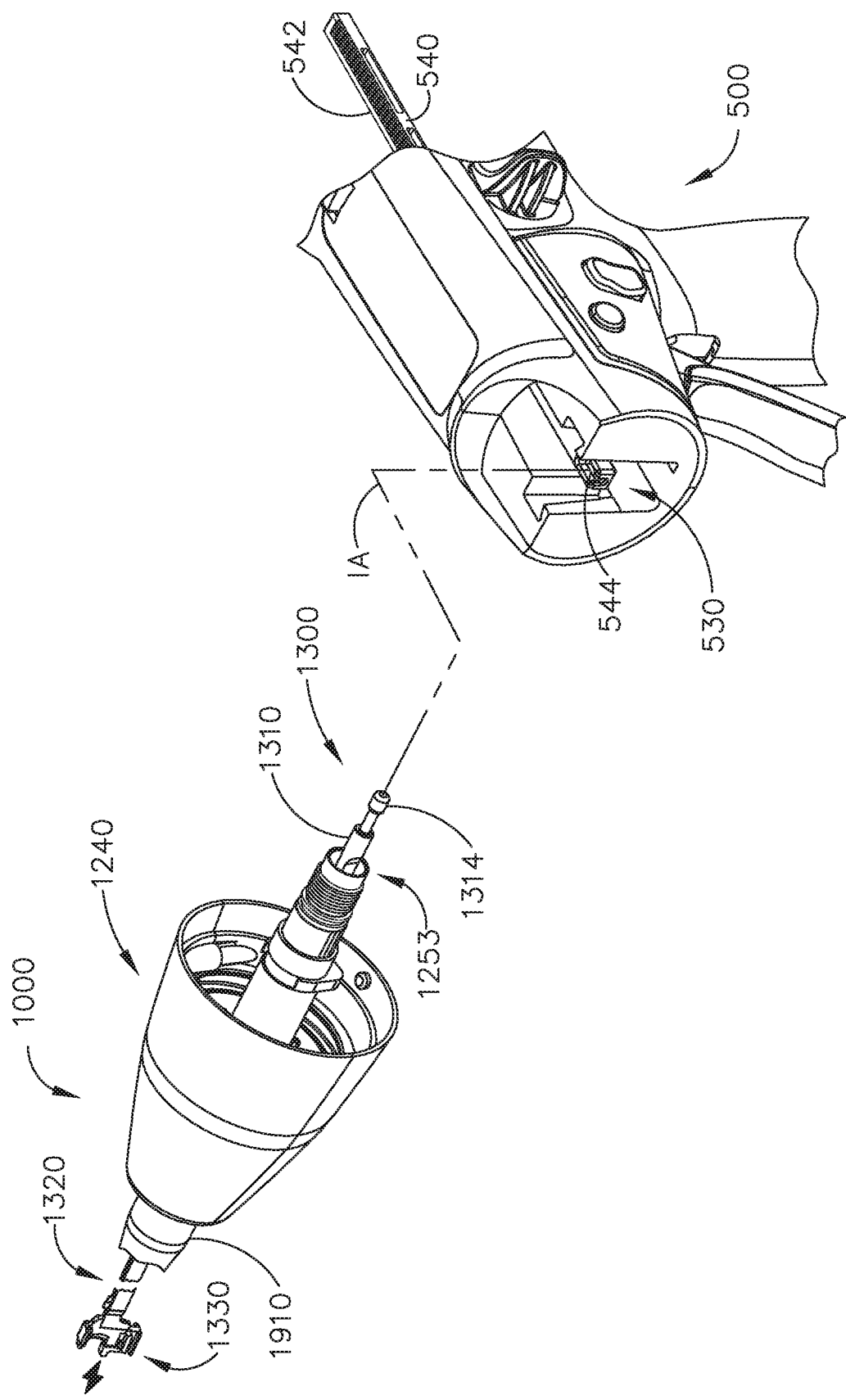
FIG. 3 is another exploded perspective assembly view of portions of the handle assembly and interchangeable surgical tool assembly of FIGS. 1 and 2 according to one aspect of this disclosure.
Figure 4:
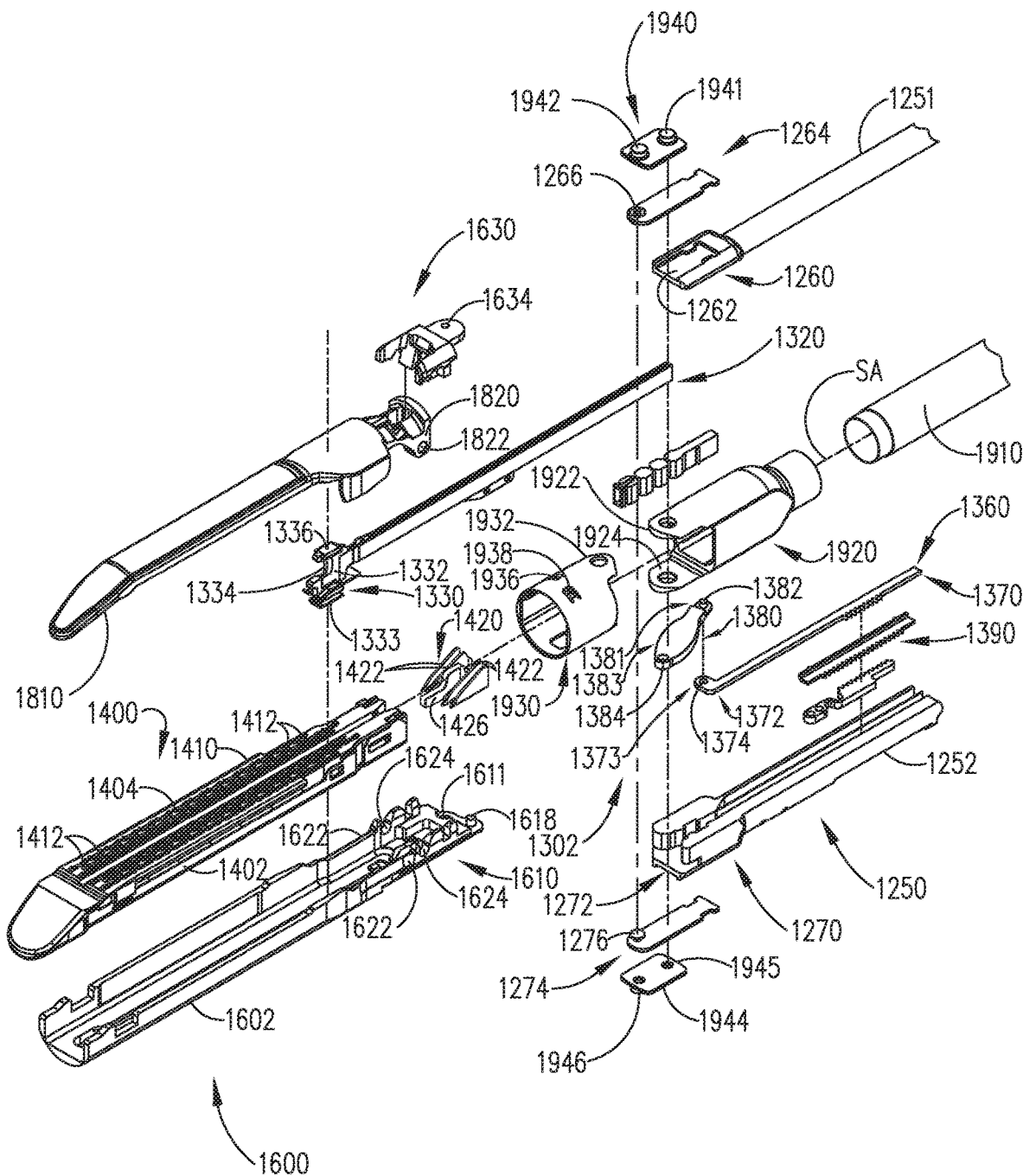
FIG. 4 is an exploded assembly view of a proximal portion of the interchangeable surgical tool assembly of FIGS. 1-3 according to one aspect of this disclosure.

Turning to FIG. 4, the articulation connector 1920 includes upper and lower tangs 1922, 1924 protrude distally from a distal end of the articulation connector 1920 to be movably coupled to an end effector closure sleeve or distal closure tube segment 1930. See FIG. 3. The distal closure tube segment 1930 includes an upper tang 1932 and a lower tang (not shown) that protrude proximally from a proximal end thereof. An upper double pivot link 1940 includes proximal and distal pins 1941, 1942 that engage corresponding holes in the upper tangs 1922, 1932 of the articulation connector 1920 and distal closure tube segment 1930, respectively. Similarly, a lower double pivot link 1944 includes proximal and distal pins 1945, 1946 that engage corresponding holes in the lower tangs 1924 of the articulation connector 1920 and distal closure tube segment 1930, respectively.

Still referring to FIG. 4, in the illustrated example, the distal closure tube segment 1930 includes positive jaw opening features or tabs 1936, 1938 that correspond with corresponding portions of the anvil 1810 to apply opening motions to the anvil 1810 as the distal closure tube segment 1930 is retracted in the proximal direction PD to a starting position. Further details regarding the opening and closing of the anvil 1810 may be found in U.S. patent application Ser. No. 15/635,621, entitled SURGICAL INSTRUMENT WITH POSITIVE JAW OPENING FEATURES, filed on Jun. 28, 2017, the entire disclosure of which is hereby incorporated by reference herein.

Figure 5:
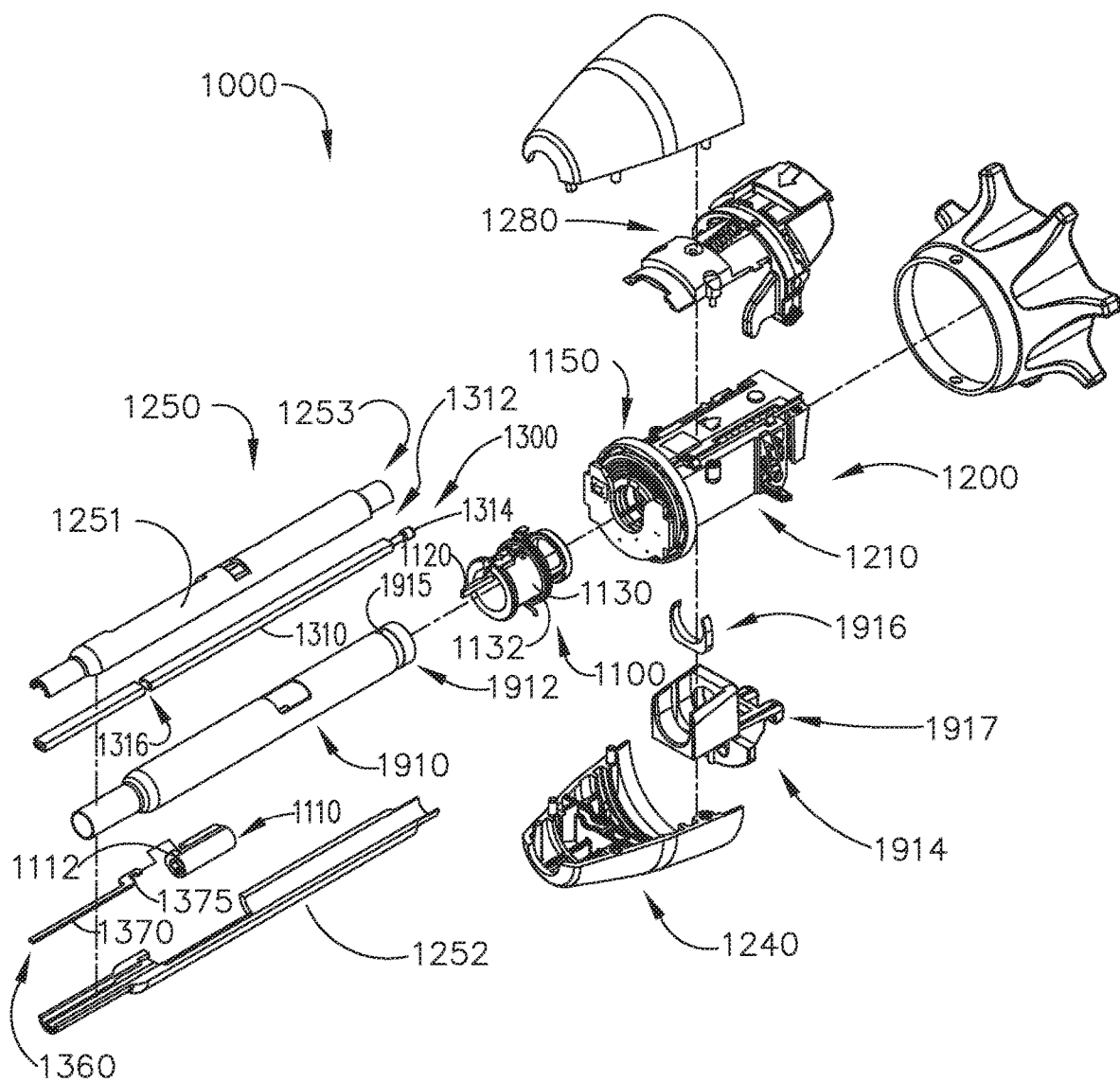
FIG. 5 is another exploded assembly view of a distal portion of the interchangeable surgical tool assembly of FIGS. 1-5 according to one aspect of this disclosure.

As shown in FIG. 5, in at least one arrangement, the interchangeable surgical tool assembly 1000 includes a tool frame assembly 1200 that comprises a tool chassis 1210 that operably supports a nozzle assembly 1240 thereon. As further discussed in detail in U.S. patent application Ser. No. 15/635,631, entitled SURGICAL INSTRUMENT WITH AXIALLY MOVABLE CLOSURE MEMBER, filed on Jun. 28, 2017, and which is hereby incorporated by reference in its entirety herein, the tool chassis 1210 and nozzle arrangement 1240 facilitate rotation of the surgical end effector 1500 about a shaft axis SA relative to the tool chassis 1210. Such rotational travel is represented by arrow R in FIG. 1. As also shown in FIGS. 4 and 5, the interchangeable surgical tool assembly 1000 includes a spine assembly 1250 that operably supports the proximal closure tube 1910 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis such that the spine assembly 1250 may be selectively rotated about a shaft axis SA relative to the tool chassis 1210.

As shown in FIG. 4, the upper spine segment 1251 terminates in an upper lug mount feature 1260 and the lower spine segment 1252 terminates in a lower lug mount feature 1270. The upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis SA. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. The lower pivot pin 1276 as well as the pivot hole 1611 is offset from the shaft axis SA. The lower pivot pin 1276 is vertically aligned with the pivot socket 1266 to define the articulation axis AA about which the surgical end effector 1500 may articulate relative to the shaft axis SA. See FIG. 1. Although the articulation axis AA is transverse to the shaft axis SA, in at least one arrangement, the articulation axis AA is laterally offset therefrom and does not intersect the shaft axis SA.

Turning to FIG. 5, a proximal end 1912 of the proximal closure tube 1910 is rotatably coupled to a closure shuttle 1914 by a connector 1916 that is seated in an annular groove 1915 in the proximal closure tube segment 1910. The closure shuttle 1914 is supported for axial travel within the tool chassis 1210 and has a pair of hooks 1917 thereon configured to engage the closure drive system 510 when the tool chassis 1210 is coupled to the handle frame 506. The tool chassis 1210 further supports a latch assembly 1280 for releasably latching the tool chassis 1210 to the handle frame 506. Further details regarding the tool chassis 1210 and latch assembly 1280 may be found in U.S. patent application Ser. No. 15/635,631, entitled SURGICAL INSTRUMENT WITH AXIALLY MOVABLE CLOSURE MEMBER, filed on Jun. 28, 2017, and which is the entire disclosure of which is hereby incorporated by reference herein.

The firing drive system 530 in the handle assembly 500 is configured to be operably coupled to a firing system 1300 that is operably supported in the interchangeable surgical tool assembly 1000. The firing system 1300 may include an intermediate firing shaft portion 1310 that is configured to be axially moved in the distal and proximal directions in response to corresponding firing motions applied thereto by the firing drive system 530. See FIG. 4. As shown in FIG. 5, a proximal end 1312 of the intermediate firing shaft portion 1310 has a firing shaft attachment lug 1314 formed thereon that is configured to be seated into an attachment cradle 544 (FIG. 3) that is on the distal end of the longitudinally movable drive member 540 of the firing drive system 530 within the handle assembly 500. Such arrangement facilitates the axial movement of the intermediate firing shaft portion 1310 upon actuation of the firing drive system 530. In the illustrated example, the intermediate firing shaft portion 1310 is configured for attachment to a distal cutting portion or knife bar 1320. As shown in FIG. 4, the knife bar 1320 is connected to a firing member or knife member 1330. The knife member 1330 comprises a knife body 1332 that operably supports a tissue cutting blade 1334 thereon. The knife body 1332 may further include anvil engagement tabs or features 1336 and channel engagement features or a foot 1338. The anvil engagement features 1336 may serve to apply additional closure motions to the anvil 1810 as the knife member 1330 is advanced distally through the end effector 1500.

In the illustrated example, the surgical end effector 1500 is selectively articulatable about the articulation axis AA by an articulation system 1360. In one form, the articulation system 1360 includes proximal articulation driver 1370 that is pivotally coupled to an articulation link 1380. As can be most particularly seen in FIG. 4, an offset attachment lug 1373 is formed on a distal end 1372 of the proximal articulation driver 1370. A pivot hole 1374 is formed in the offset attachment lug 1373 and is configured to pivotally receive therein a proximal link pin 1382 formed on the proximal end 1381 of the articulation link 1380. A distal end 1383 of the articulation link 1380 includes a pivot hole 1384 that is configured to pivotally receive therein a channel pin 1618 formed on the proximal end portion 1610 of the elongate channel 1602. Thus, axial movement of proximal articulation driver 1370 will thereby apply articulation motions to the elongate channel 1602 to thereby cause the surgical end effector 1500 to articulate about the articulation axis AA relative to the spine assembly 1250. In various circumstances, the proximal articulation driver 1370 can be held in position by an articulation lock 1390 when the proximal articulation driver 1370 is not being moved in the proximal or distal directions. Further details regarding an example form of articulation lock 1390 may be found in U.S. patent application Ser. No. 15/635,837, entitled SURGICAL INSTRUMENT COMPRISING AN ARTICULATION SYSTEM LOCKABLE TO A FRAME, filed on Jun. 28, 2017, the entire disclosure of which is hereby incorporated by reference herein.

Further to the above, the interchangeable surgical tool assembly 1000 can include a shifter assembly 1100 which can be configured to selectively and releasably couple the proximal articulation driver 1310 to the firing system 1300. As illustrated in FIG. 5, for example, in one form, the shifter assembly 1100 includes a lock collar, or lock sleeve 1110, positioned around the intermediate firing shaft portion 1310 of the firing system 1300 wherein the lock sleeve 1110 can be rotated between an engaged position in which the lock sleeve 1110 operably couples the proximal articulation driver 1370 to the firing member assembly 1300 and a disengaged position in which the proximal articulation driver 1370 is not operably coupled to the firing member assembly 1300. When lock sleeve 1110 is in its engaged position, distal movement of the firing member assembly 1300 can move the proximal articulation driver 1370 distally and, correspondingly, proximal movement of the firing member assembly 1300 can move the proximal articulation driver 1370 proximally. When lock sleeve 1110 is in its disengaged position, movement of the firing member assembly 1300 is not transmitted to the proximal articulation driver 1370 and, as a result, the firing member assembly 1300 can move independently of the proximal articulation driver 1370. In various circumstances, the proximal articulation driver 1370 can be held in position by the articulation lock 1390 when the proximal articulation driver 1370 is not being moved in the proximal or distal directions by the firing member assembly 1300.

In the illustrated arrangement, the intermediate firing shaft portion 1310 of the firing member assembly 1300 is formed with two opposed flat sides with a drive notch 1316 formed therein. See FIG. 5. As can also be seen in FIG. 5, the lock sleeve 1110 comprises a cylindrical, or an at least substantially cylindrical, body that includes a longitudinal aperture that is configured to receive the intermediate firing shaft portion 1310 therethrough. The lock sleeve 1110 can comprise diametrically-opposed, inwardly-facing lock protrusions that, when the lock sleeve 1110 is in one position, are engagingly received within corresponding portions of the drive notch 1316 in the intermediate firing shaft portion 1310 and, when in another position, are not received within the drive notch 1316 to thereby permit relative axial motion between the lock sleeve 1110 and the intermediate firing shaft 1310. As can be further seen in FIG. 5, the lock sleeve 1110 further includes a lock member 1112 that is sized to be movably received within a notch 1375 in a proximal end of the proximal articulation driver 1370. Such arrangement permits the lock sleeve 1110 to slightly rotate into and out of engagement with the intermediate firing shaft portion 1310 while remaining in position for engagement or in engagement with the notch 1375 in the proximal articulation driver 1370. For example, when the lock sleeve 1110 is in its engaged position, the lock protrusions are positioned within the drive notch 1316 in the intermediate firing shaft portion 1310 such that a distal pushing force and/or a proximal pulling force can be transmitted from the firing member assembly 1300 to the lock sleeve 1110. Such axial pushing or pulling motion is then transmitted from the lock sleeve 1110 to the proximal articulation driver 1370 to thereby articulate the surgical end effector 1500. In effect, the firing member assembly 1300, the lock sleeve 1110, and the proximal articulation driver 1370 will move together when the lock sleeve 1110 is in its engaged (articulation) position. On the other hand, when the lock sleeve 1110 is in its disengaged position, the lock protrusions are not received within the drive notch 1316 in the intermediate firing shaft portion 1310 and, as a result, a distal pushing force and/or a proximal pulling force may not be transmitted from the firing member assembly 1300 to the lock sleeve 1110 (and the proximal articulation driver 1370).

In the illustrated example, relative movement of the lock sleeve 1110 between its engaged and disengaged positions may be controlled by the shifter assembly 1100 that interfaces with the proximal closure tube 1910. Still referring to FIG. 5, the shifter assembly 1100 further includes a shifter key 1120 that is configured to be slidably received within a key groove formed in the outer perimeter of the lock sleeve 1110. Such arrangement enables the shifter key 1120 to move axially with respect to the lock sleeve 1110. As discussed in further detail in U.S. patent application Ser. No. 15/635,631, entitled SURGICAL INSTRUMENT WITH AXIALLY MOVABLE CLOSURE MEMBER filed on Jun. 28, 2017, the entire disclosure of which is hereby incorporated by reference herein, a portion of the shifter key 1120 is configured to cammingly interact with a cam opening (not shown) in the proximal closure tube portion 1910. Also in the illustrated example, the shifter assembly 1100 further includes a switch drum 1130 that is rotatably received on a proximal end portion of the proximal closure tube portion 1910. A portion of the shifter key 1120 extends through an axial slot segment in the switch drum 1130 and is movably received within an arcuate slot segment in the switch drum 1130. A switch drum torsion spring 1132 is mounted on the switch drum 1130 and engages a portion of the nozzle assembly 1240 to apply a torsional bias or rotation which serves to rotate the switch drum 1130 until the portion of the shifter key 1120 reaches an end portion of the cam opening in the proximal closure tube portion 1910. When in this position, the switch drum 1130 may provide a torsional bias to the shifter key 1120 which thereby causes the lock sleeve 1110 to rotate into its engaged position with the intermediate firing shaft portion 1310. This position also corresponds to the unactuated configuration of the proximal closure tube 1910 (and distal closure tube segment 1930).

In one arrangement, for example, when the proximal closure tube 1910 is in an unactuated configuration (anvil 1810 is in an open position spaced away from the cartridge mounted in the elongate channel 1602) actuation of the intermediate firing shaft portion 1310 will result in the axial movement of the proximal articulation driver 1370 to facilitate articulation of the end effector 1500. Once the user has articulated the surgical end effector 1500 to a desired orientation, the user may then actuate the proximal closure tube portion 1910. Actuation of the proximal closure tube portion 1910 will result in the distal travel of the distal closure tube segment 1930 to ultimately apply a closing motion to the anvil 1810. This distal travel of the proximal closure tube portion 1910 will result in the cam opening therein cammingly interacting with a cam portion of the shifter key 1120 to thereby cause the shifter key 1120 to rotate the lock sleeve 1110 in an actuation direction. Such rotation of the lock sleeve 1110 will result in the disengagement of the lock protrusions from the drive notch 1316 in the intermediate firing shaft portion 1310. When in such configuration, the firing drive system 530 may be actuated to actuate the intermediate firing shaft portion 1310 without actuating the proximal articulation driver 1370. Further details concerning the operation of the switch drum 1130 and lock sleeve 1110, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, the entire disclosures of which are hereby incorporated by reference herein.

Figure 15:
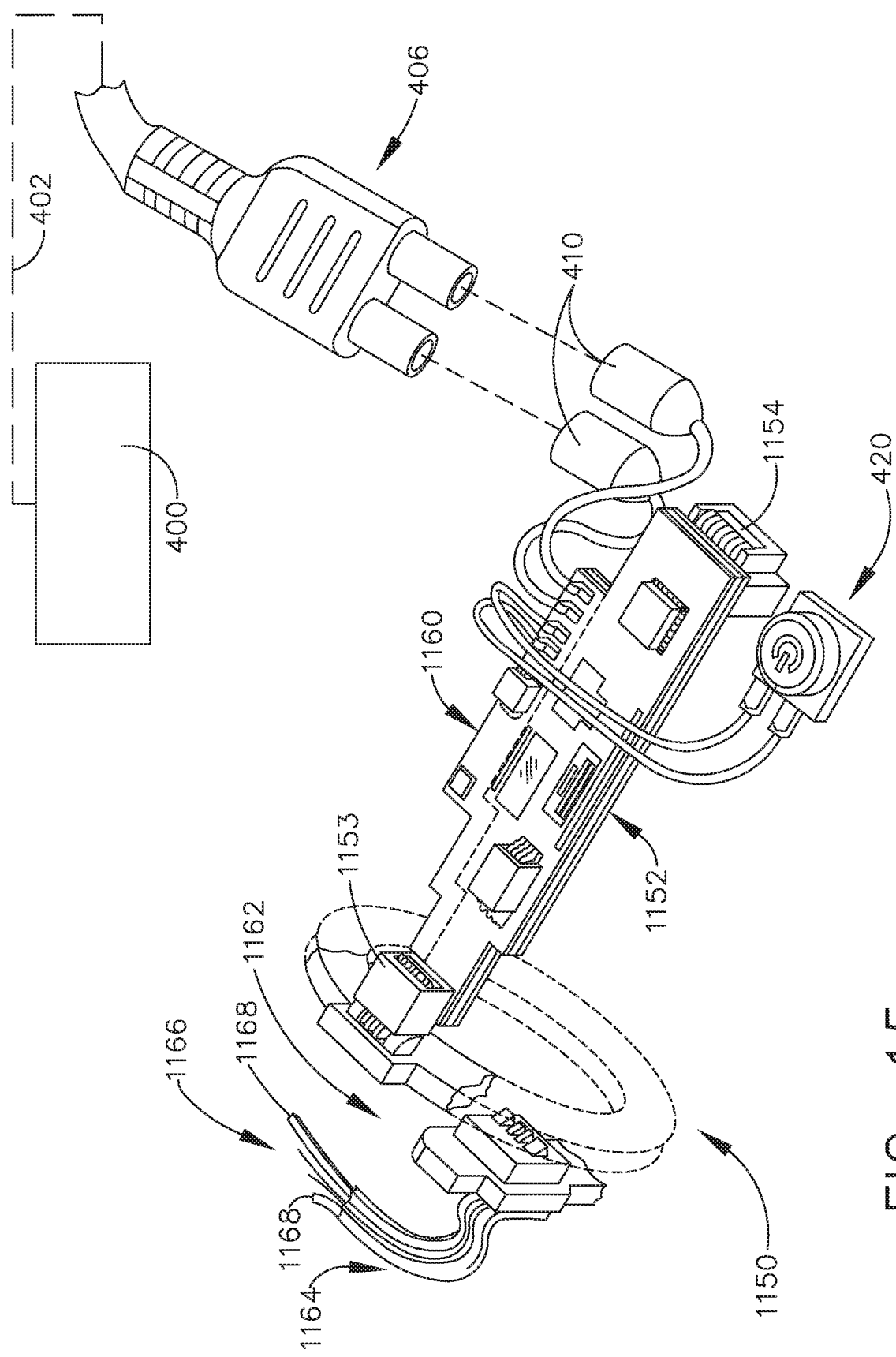
FIG. 15 is a perspective view of an onboard circuit board arrangement and RF generator plus configuration according to one aspect of this disclosure.

As also illustrated in FIGS. 5 and 15, the interchangeable surgical tool assembly 1000 can comprise a slip ring assembly 1150 which can be configured to conduct electrical power to and/or from the surgical end effector 1500 and/or communicate signals to and/or from the surgical end effector 1500, back to an onboard circuit board 1152, while facilitating rotational travel of the shaft and end effector 1500 about the shaft axis SA relative to the tool chassis 1210 by rotating the nozzle assembly 1240. As shown in FIG. 15, in at least one arrangement, the onboard circuit board 1152 includes an onboard connector 1154 that is configured to interface with a housing connector 562 (FIG. 9) communicating with a microprocessor 560 that is supported in the handle assembly 500 or robotic system controller, for example. The slip ring assembly 1150 is configured to interface with a proximal connector 1153 that interfaces with the onboard circuit board 1152. Further details concerning the slip ring assembly 1150 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

An example version of the interchangeable surgical tool assembly 1000 disclosed herein may be employed in connection with a standard (mechanical) surgical fastener cartridge 1400 or a cartridge 1700 that is configured to facilitate cutting of tissue with the knife member and seal the cut tissue using radio frequency (RF) energy. Turning again to FIG. 4, a conventional or standard mechanical-type cartridge 1400 is depicted. Such cartridge arrangements are known and may comprise a cartridge body 1402 that is sized and shaped to be removably received and supported in the elongate channel 1602. For example, the cartridge body 1402 may be configured to be removably retained in snap engagement with the elongate channel 1602. The cartridge body 1402 includes an elongate slot 1404 to accommodate axial travel of the knife member 1330 therethrough. The cartridge body 1402 operably supports therein a plurality of staple drivers (not shown) that are aligned in rows on each side of the centrally disposed elongate slot 1404. The drivers are associated with corresponding staple/fastener pockets 1412 that open through the upper deck surface 1410 of the cartridge body 1402. Each of the staple drivers supports one or more surgical staple or fastener (not shown) thereon. A sled assembly 1420 is supported within a proximal end of the cartridge body 1402 and is located proximal to the drivers and fasteners in a starting position when the cartridge 1400 is new and unfired. The sled assembly 1420 includes a plurality of sloped or wedge-shaped cams 1422 wherein each cam 1422 corresponds to a particular line of fasteners or drivers located on a side of the slot 1404. The sled assembly 1420 is configured to be contacted and driven by the knife member 1330 as the knife member is driven distally through the tissue that is clamped between the anvil and the cartridge deck surface 1410. As the drivers are driven upward toward the cartridge deck surface 1410, the fastener(s) supported thereon are driven out of their staple pockets 1412 and through the tissue that is clamped between anvil and the cartridge.

Figure 7:
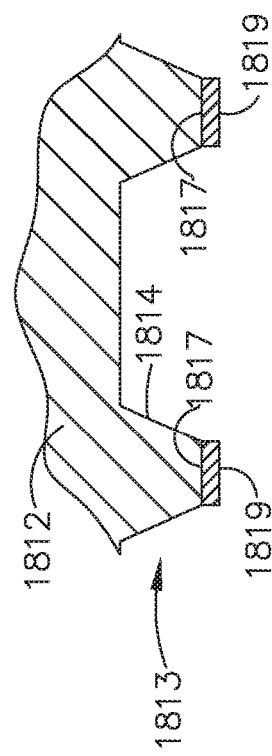
FIG. 7 is a partial cross-sectional view of the anvil of FIG. 6 according to one aspect of this disclosure.
Figure 6:
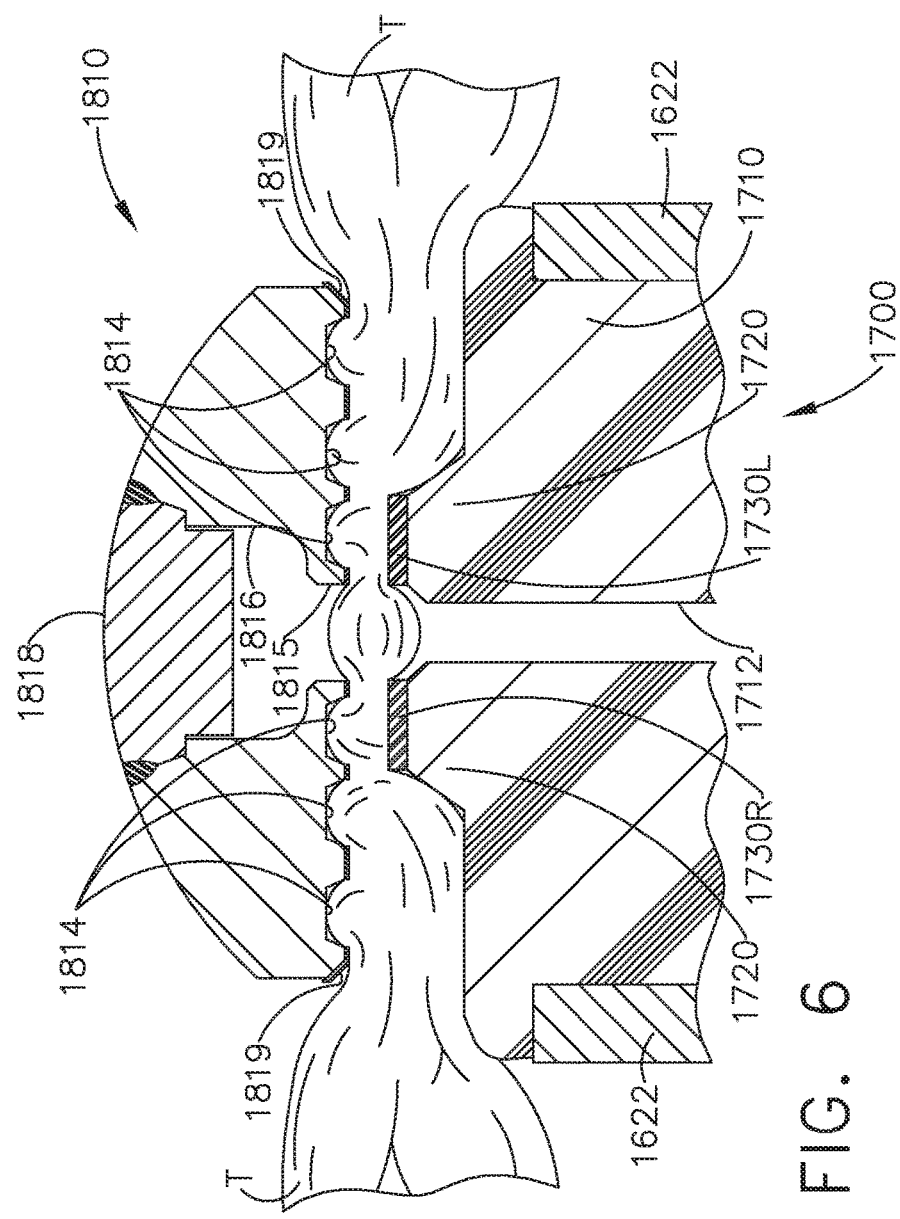
FIG. 6 is a partial cross-sectional view of the end effector depicted in FIGS. 1-5 supporting an RF cartridge therein and with tissue clamped between the cartridge and the anvil according to one aspect of this disclosure.

Still referring to FIG. 4, the anvil 1810 in at least one form includes an anvil mounting portion 1820 that has a pair of anvil trunnions 1822 protruding laterally therefrom to be pivotally received in corresponding trunnion cradles 1614 formed in the upstanding walls 1622 of the proximal end portion 1610 of the elongate channel 1602. The anvil trunnions 1822 are pivotally retained in their corresponding trunnion cradle 1614 by the channel cap or anvil retainer 1630. The anvil mounting portion 1820 is movably or pivotably supported on the elongate channel 1602 for selective pivotal travel relative thereto about a fixed anvil pivot axis that is transverse to the shaft axis SA. As shown in FIGS. 6 and 7, in at least one form, the anvil 1810 includes an anvil body portion 1812 that is fabricated from an electrically conductive metal material for example and has a staple forming undersurface 1813 that has a series of fastener forming pockets 1814 formed therein on each side of a centrally disposed anvil slot 1815 that is configured to slidably accommodate the knife member 1330 therein. The anvil slot 1815 opens into an upper opening 1816 that extends longitudinally through the anvil body 1812 to accommodate the anvil engagement features 1336 on the knife member 1330 during firing. When a conventional mechanical surgical staple/fastener cartridge 1400 is installed in the elongate channel 1602, the staples/fasteners are driven through the tissue T and into forming contact with the corresponding fastener forming pockets 1814. The anvil body 1812 may have an opening in the upper portion thereof to facilitate ease of installation for example. An anvil cap 1818 may be inserted therein and welded to the anvil body 1812 to enclose the opening and improve the overall stiffness of the anvil body 1812. As shown in FIG. 7, to facilitate use of the end effector 1500 in connection with RF cartridges 1700, the tissue facing segments 1817 of the fastener forming undersurface 1813 may have electrically insulative material 1819 thereon.

Figure 8:
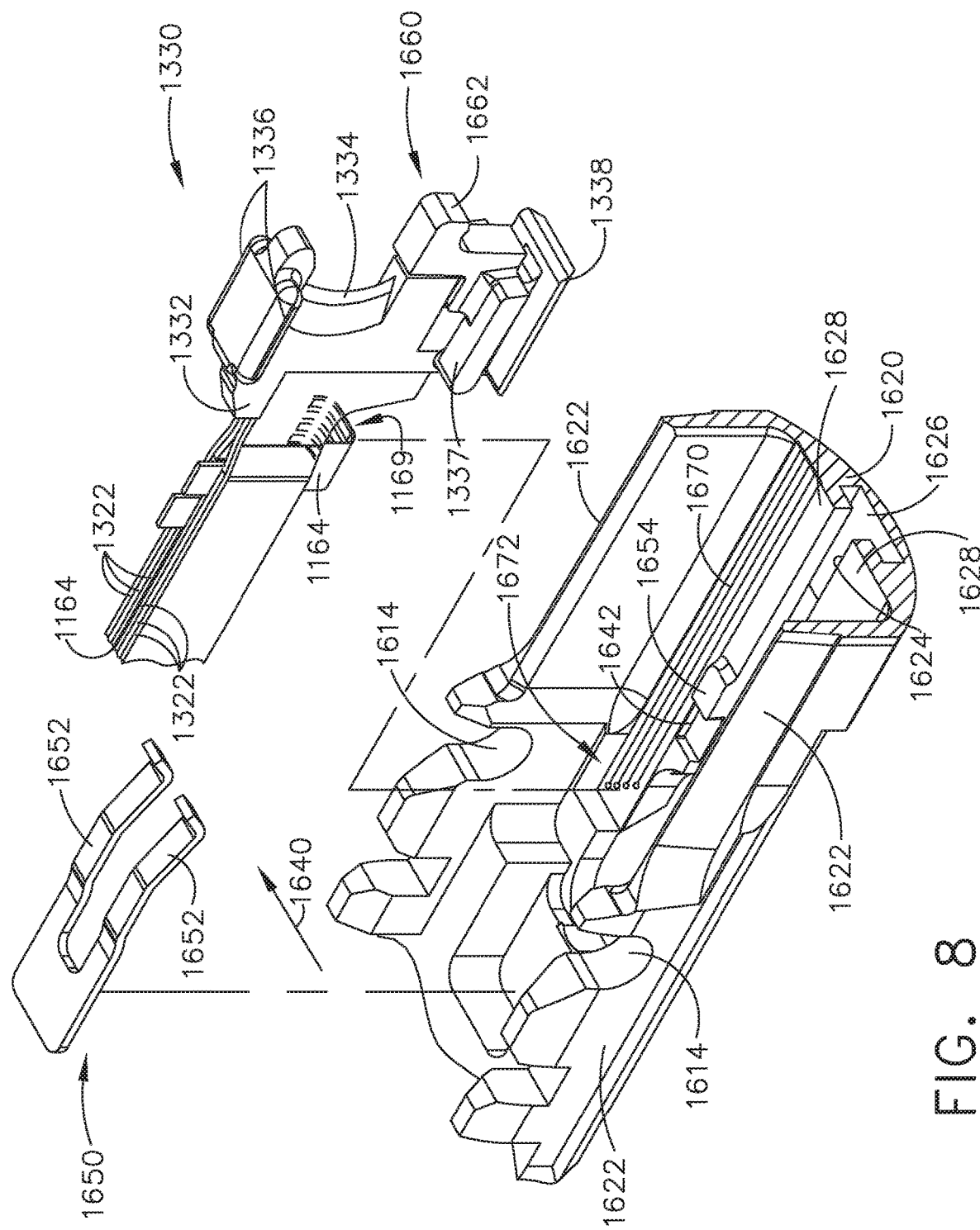
FIG. 8 is another exploded assembly view of a portion of the interchangeable surgical tool assembly of FIGS. 1-5 according to one aspect of this disclosure.

In the illustrated arrangement, the interchangeable surgical tool assembly 1000 is configured with a firing member lockout system, generally designated as 1640. See FIG. 8. As shown in FIG. 8, the elongate channel 1602 includes a bottom surface or bottom portion 1620 that has two upstanding side walls 1622 protruding therefrom. A centrally disposed longitudinal channel slot 1624 is formed through the bottom portion 1620 to facilitate the axial travel of the knife member 1330 therethrough. The channel slot 1624 opens into a longitudinal passage 1626 that accommodates the channel engagement feature or foot 1338 on the knife member 1330. The passage 1626 serves to define two inwardly extending ledge portions 1628 that serve to engage corresponding portions of the channel engagement feature or foot 1338. The firing member lockout system 1640 includes proximal openings 1642 located on each side of the channel slot 1624 that are each configured to receive corresponding portions of the channel engagement feature or foot 1338 when the knife member 1330 is in a starting position. A knife lockout spring 1650 is supported in the proximal end 1610 of the elongate channel 1602 and serves to bias the knife member 1330 downward. As shown in FIG. 8, the knife lockout spring 1650 includes two distally ending spring arms 1652 that are configured to engage corresponding central channel engagement features 1337 on the knife body 1332. The spring arms 1652 are configured to bias the central channel engagement features 1337 downward. Thus, when in the starting (unfired position), the knife member 1330 is biased downward such that the channel engagement features or foot 1338 is received within the corresponding proximal openings 1642 in the elongate 1602 channel. When in that locked position, if one were to attempt to distally advance the knife 1330, the central channel engagement features 1137 and/or foot 1338 would engage upstanding ledges 1654 on the elongate channel 1602 (FIGS. 8 and 11) and the knife 1330 could not be fired.

Still referring to FIG. 8, the firing member lockout system 1640 also includes an unlocking assembly 1660 formed or supported on a distal end of the firing member body 1332. The unlocking assembly 1660 includes a distally extending ledge 1662 that is configured to engage an unlocking feature 1426 formed on the sled assembly 1420 when the sled assembly 1420 is in its starting position in an unfired surgical staple cartridge 1400. Thus, when an unfired surgical staple cartridge 1400 is properly installed in the elongate channel 1602, the ledge 1662 on the unlocking assembly 1660 contacts the unlocking feature 1426 on the sled assembly 1420 which serves to bias the knife member 1330 upward such that the central channel engagement features 1137 and/or foot 1338 clear the upstanding ledges 1654 in the channel bottom 1620 to facilitate axial passage of the knife member 1330 through the elongate channel 1602. If a partially fired cartridge 1400 is unwittingly installed in the elongate channel, the sled assembly 1420 will not be in the starting position and the knife member 1330 will remain in the locked position.

Figure 9:
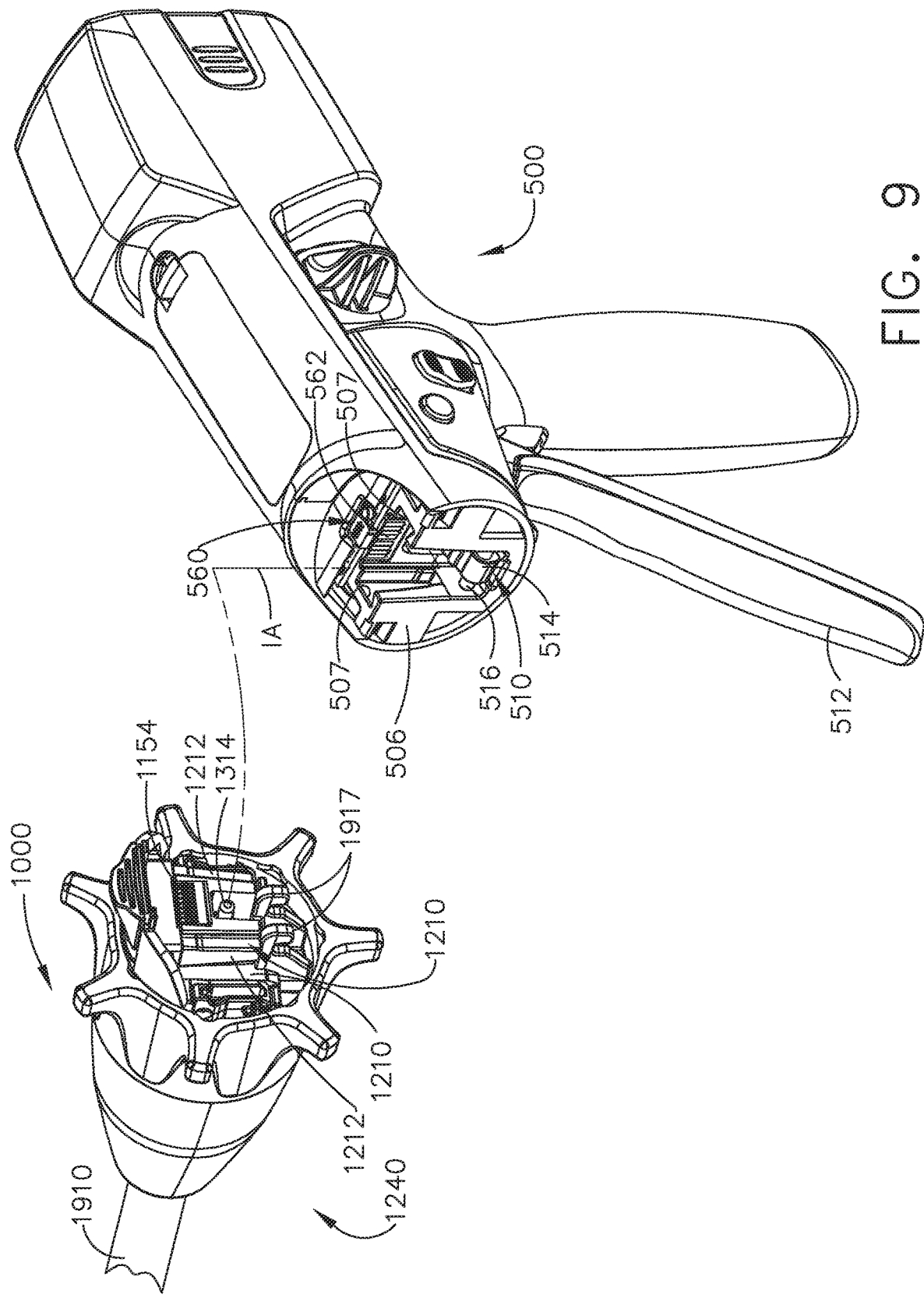
FIG. 9 is another exploded assembly view of the interchangeable surgical tool assembly and handle assembly of FIGS. 1 and 2 according to one aspect of this disclosure.

Attachment of the interchangeable surgical tool assembly 1000 to the handle assembly 500 will now be described with reference to FIGS. 3 and 9. To commence the coupling process, the clinician may position the tool chassis 1210 of the interchangeable surgical tool assembly 1000 above or adjacent to the distal end of the handle frame 506 such that tapered attachment portions 1212 formed on the tool chassis 1210 are aligned with dovetail slots 507 in the handle frame 506. The clinician may then move the surgical tool assembly 1000 along an installation axis IA that is perpendicular to the shaft axis SA to seat the tapered attachment portions 1212 in "operable engagement" with the corresponding dovetail receiving slots 507 in the distal end of the handle frame 506. In doing so, the firing shaft attachment lug 1314 on the intermediate firing shaft portion 1310 will also be seated in the cradle 544 in the longitudinally movable drive member 540 within the handle assembly 500 and the portions of a pin 516 on a closure link 514 will be seated in the corresponding hooks 1917 in the closure shuttle 1914. As used herein, the term "operable engagement" in the context of two components means that the two components are sufficiently engaged with each other so that upon application of an actuation motion thereto, the components may carry out their intended action, function and/or procedure. Also during this process, the onboard connector 1154 on the surgical tool assembly 1000 is coupled to the housing connector 562 that communicates with the microprocessor 560 that is supported in the handle assembly 500 or robotic system controller, for example.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis SA (unarticulated state). Once the surgical end effector 1500 has passed through the trocar port, for example, the clinician may need to articulate the end effector 1500 to advantageously position it adjacent the target tissue. This is prior to closing the anvil 1810 onto the target tissue, so the closure drive system 510 would remain unactuated. When in this position, actuation of the firing drive system 530 will result in the application of articulation motions to the proximal articulation driver 1370. Once the end effector 1500 has attained the desired articulated position, the firing drive system 530 is deactivated and the articulation lock 1390 may retain the surgical end effector 1500 in the articulated position. The clinician may then actuate the closure drive system 510 to close the anvil 1810 onto the target tissue. Such actuation of the closure drive system 510 may also result in the shifter assembly 1100 delinking the proximal articulation driver 1370 from the intermediate firing shaft portion 1310. Thus, once the target tissue has been captured in the surgical end effector 1500, the clinician may once again actuate the firing drive system 530 to axially advance the firing member 1330 through the surgical staple/fastener cartridge 1400 or RF cartridge 1700 to cut the clamped tissue and fire the staples/fasteners into the cut tissue T. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the scope of the present disclosure.

As indicated above, the surgical tool assembly 1000 is configured to be used in connection with conventional mechanical surgical staple/fastener cartridges 1400 as well as with RF cartridges 1700. In at least one form, the RF cartridge 1700 may facilitate mechanical cutting of tissue that is clamped between the anvil 1810 and the RF cartridge 1700 with the knife member 1330 while coagulating electrical current is delivered to the tissue in the current path. Alternative arrangements for mechanically cutting and coagulating tissue using electrical current are disclosed in, for example, U.S. Pat. Nos. 5,403,312; 7,780,663 and U.S. patent application Ser. No. 15/142,609, entitled ELECTROSURGICAL INSTRUMENT WITH ELECTRICALLY CONDUCTIVE GAP SETTING AND TISSUE ENGAGING MEMBERS, the entire disclosures of each said references being incorporated by reference herein. Such instruments, may, for example, improve hemostasis, reduce surgical complexity as well as operating room time.

Figure 10:
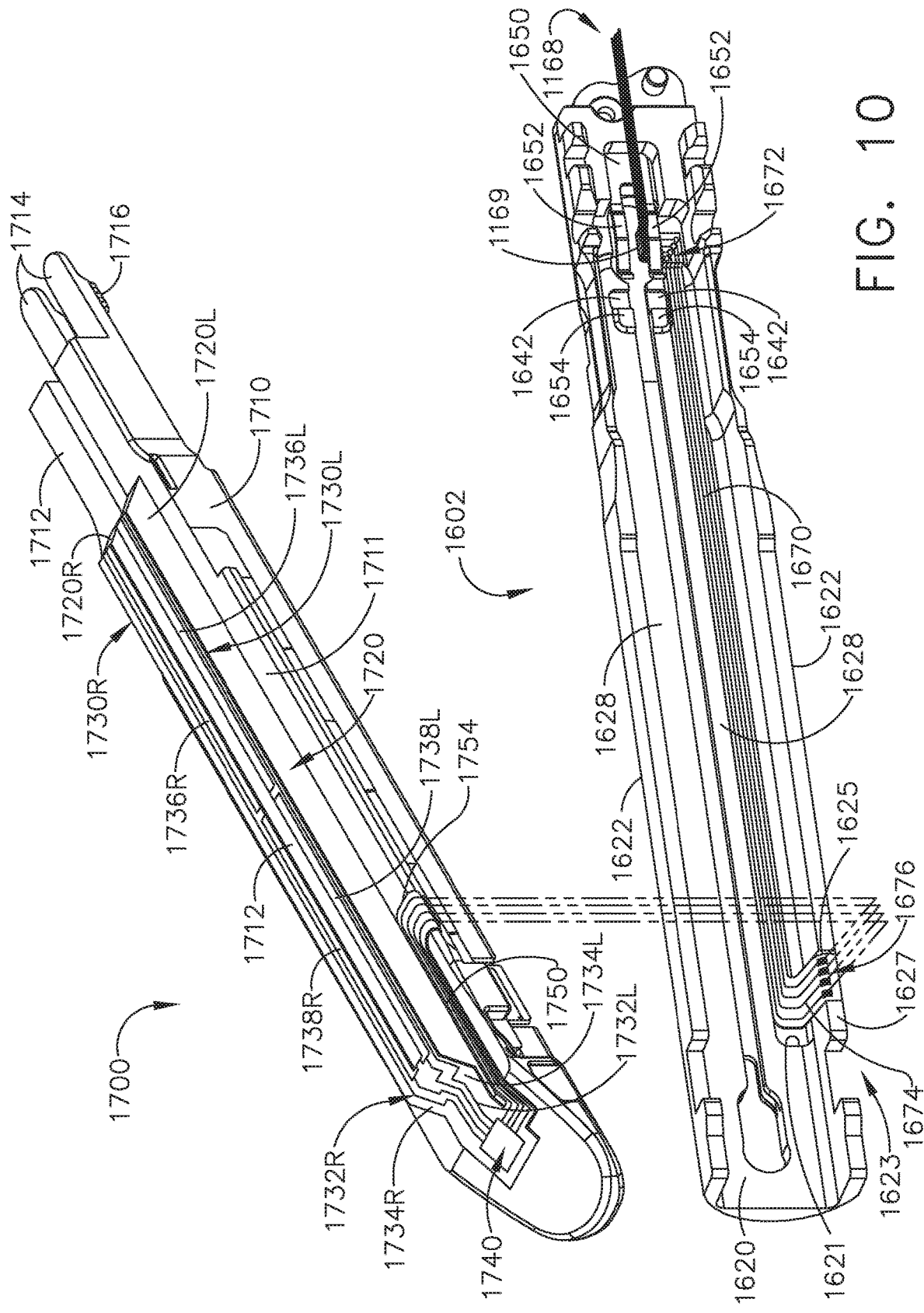
FIG. 10 is a perspective view of an RF cartridge and an elongate channel of the interchangeable surgical tool assembly of FIGS. 1-5 according to one aspect of this disclosure.
Figure 11:
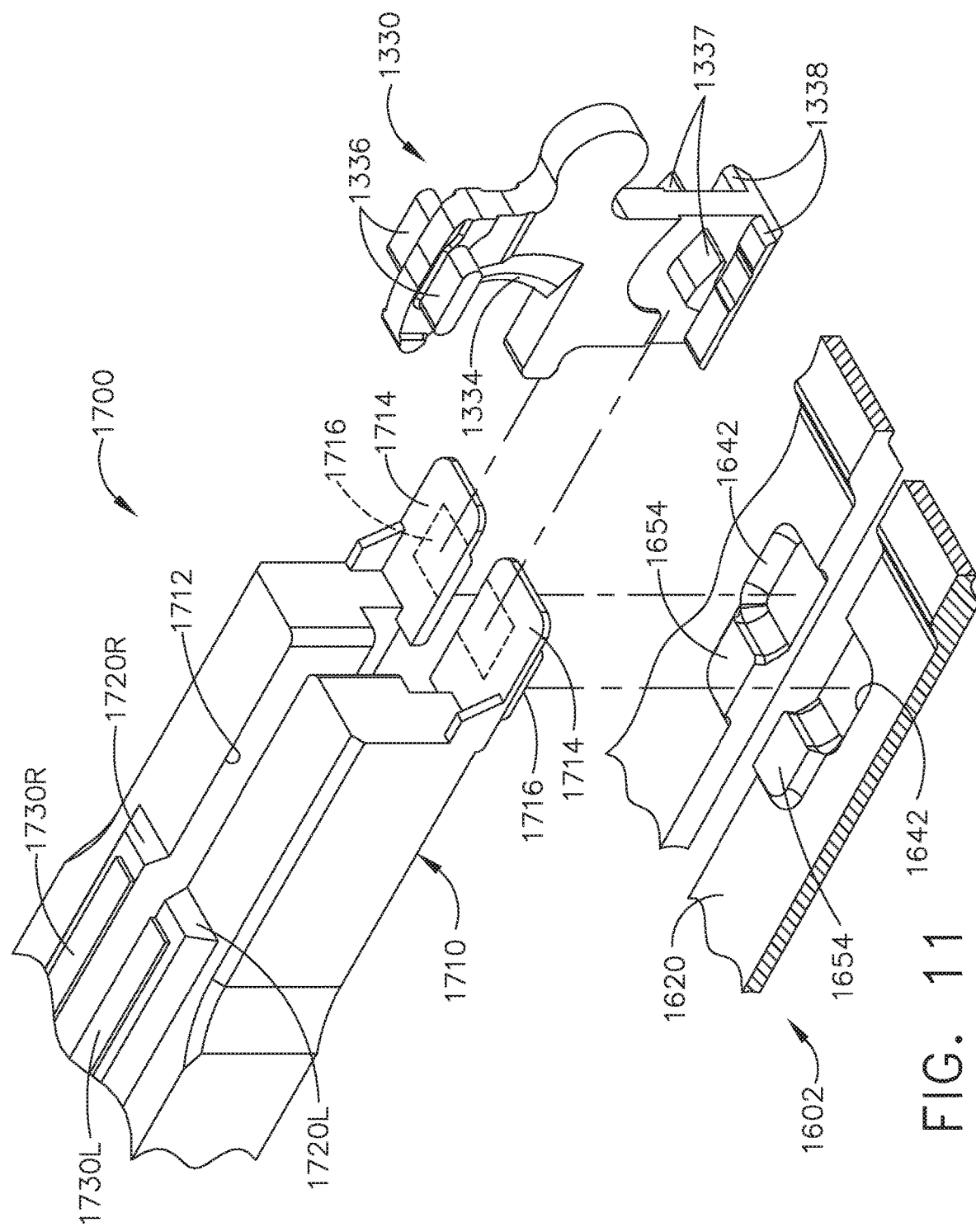
FIG. 11 is a partial perspective view of portions of the RF cartridge and elongate channel of FIG. 10 with a knife member aspect according to one aspect of this disclosure.
Figure 12:
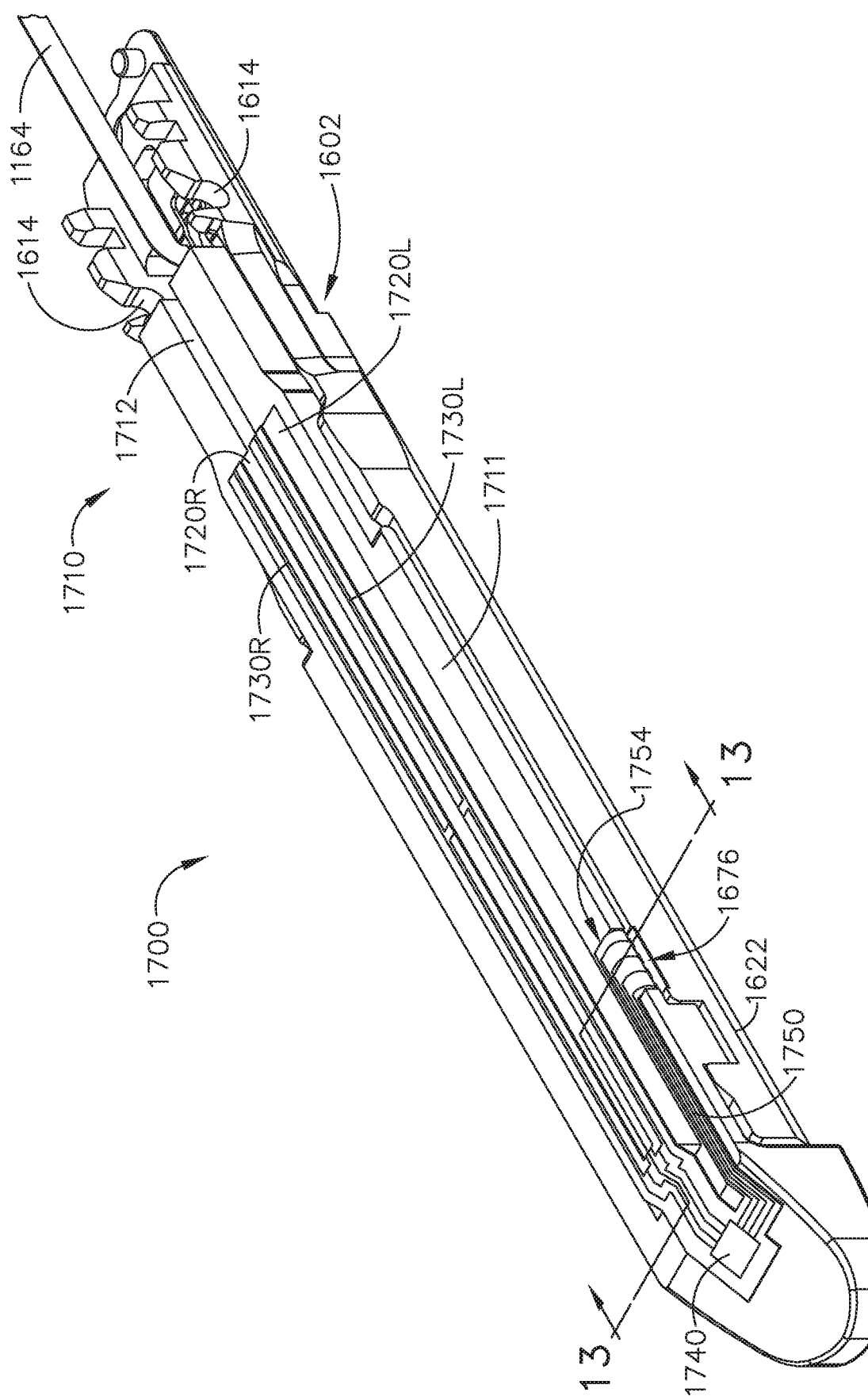
FIG. 12 is another perspective view of the RF cartridge installed in the elongate channel of FIG. 10 and illustrating a portion of a flexible shaft circuit arrangement according to one aspect of this disclosure.
Figure 13:
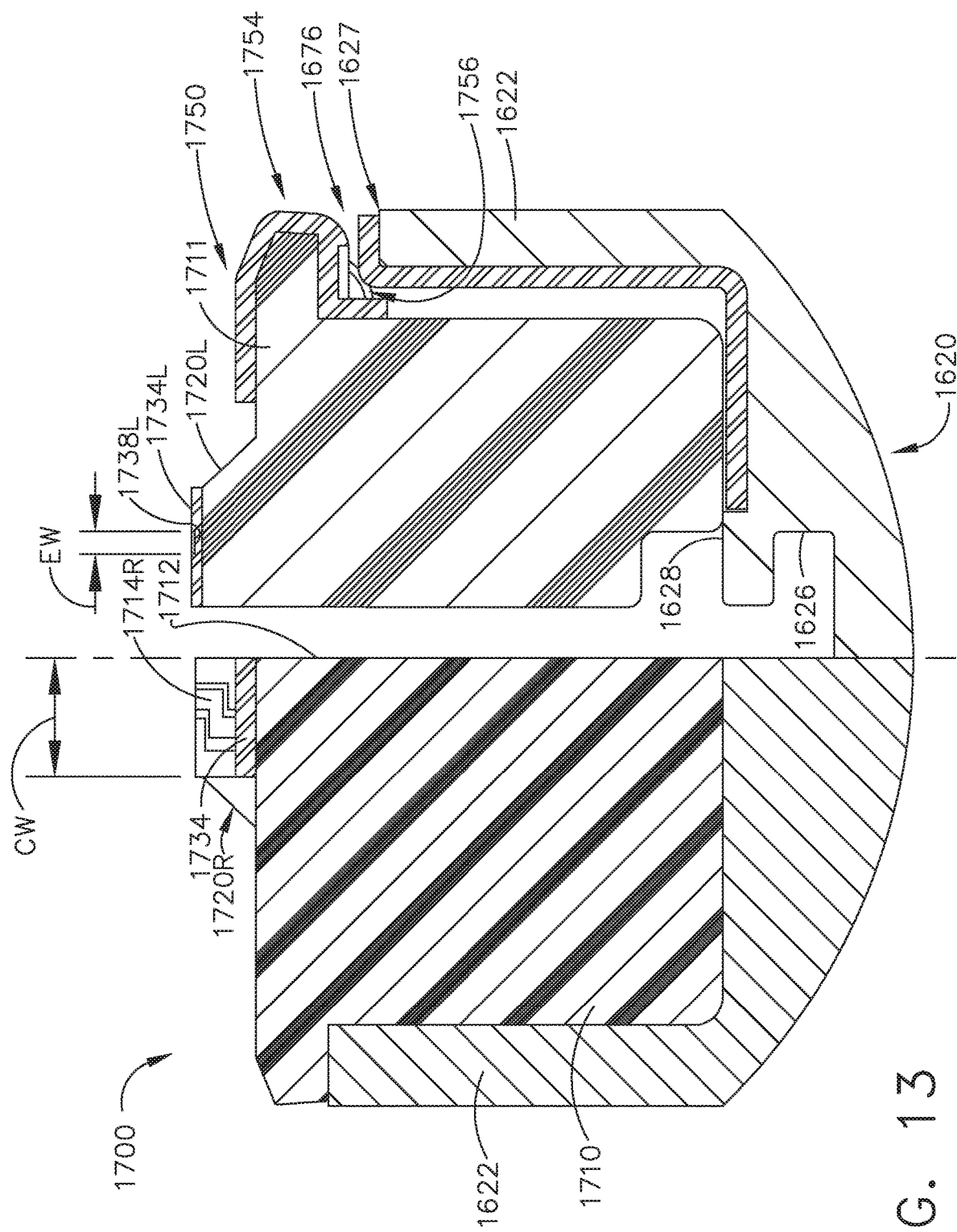
FIG. 13 is a cross-sectional end view of the RF cartridge and elongate channel of FIG. 12 taken along lines 13-13 in FIG. 12 according to one aspect of this disclosure.

As shown in FIGS. 10-12, in at least one arrangement, the RF surgical cartridge 1700 includes a cartridge body 1710 that is sized and shaped to be removably received and supported in the elongate channel 1602. For example, the cartridge body 1710 may be configured to be removably retained in snap engagement with the elongate channel 1602. In various arrangements, the cartridge body 1710 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1710 includes a centrally disposed elongate slot 1712 that extends longitudinally through the cartridge body to accommodate longitudinal travel of the knife 1330 therethrough. As shown in FIGS. 10 and 11, a pair of lockout engagement tails 1714 extend proximally from the cartridge body 1710. Each lockout engagement tail 1714 has a lockout pad 1716 formed on the underside thereof that are sized to be received within a corresponding proximal opening portion 1642 in the channel bottom 1620. Thus, when the cartridge 1700 is properly installed in the elongate channel 1602, the lockout engagement tails 1714 cover the openings 1642 and ledges 1654 to retain the knife 1330 in an unlocked position ready for firing.

Turning now to FIGS. 10-13, in the illustrated example, the cartridge body 1710 is formed with a centrally disposed raised electrode pad 1720. As can be most particularly seen in FIG. 6, the elongate slot 1712 extends through the center of the electrode pad 1720 and serves to divide the pad 1720 into a left pad segment 1720L and a right pad segment 1720R. A right flexible circuit assembly 1730R is attached to the right pad segment 1720R and a left flexible circuit assembly 1730L is attached to the left pad segment 1720L. In at least one arrangement for example, the right flexible circuit 1730R comprises a plurality of electrical conductors 1732R that may include, for example, wider electrical conductors/conductors for RF purposes and thinner electrical conductors for conventional stapling purposes that are supported or attached or embedded into a right insulator sheath/member 1734R that is attached to the right pad 1720R. In addition, the right flexible circuit assembly 1730R includes a "phase one", proximal right electrode 1736R and a "phase two" distal right electrode 1738R. Likewise, the left flexible circuit assembly 1730L comprises a plurality of electrical conductors 1732L that may include, for example, wider electrical conductors/conductors for RF purposes and thinner electrical conductors for conventional stapling purposes that are supported or attached or embedded into a left insulator sheath/member 1734L that is attached to the left pad 1720L. In addition, the left flexible circuit assembly 1730L includes a "phase one", proximal left electrode 1736L and a "phase two" distal left electrode 1738L. The left and right electrical conductors 1732L, 1732R are attached to a distal micro-chip 1740 mounted to the distal end portion of the cartridge body 1710. In one arrangement, for example, each of the right and left flexible circuits 1730R, 1730L may have an overall width "CW" of approximately 0.025 inches and each of the electrodes 1736R, 1736L, 1738R, 1738R has a width "EW" of approximately 0.010 inches for example. See FIG. 13. However, other widths/sizes are contemplated and may be employed in alternative aspects.

Figure 14:
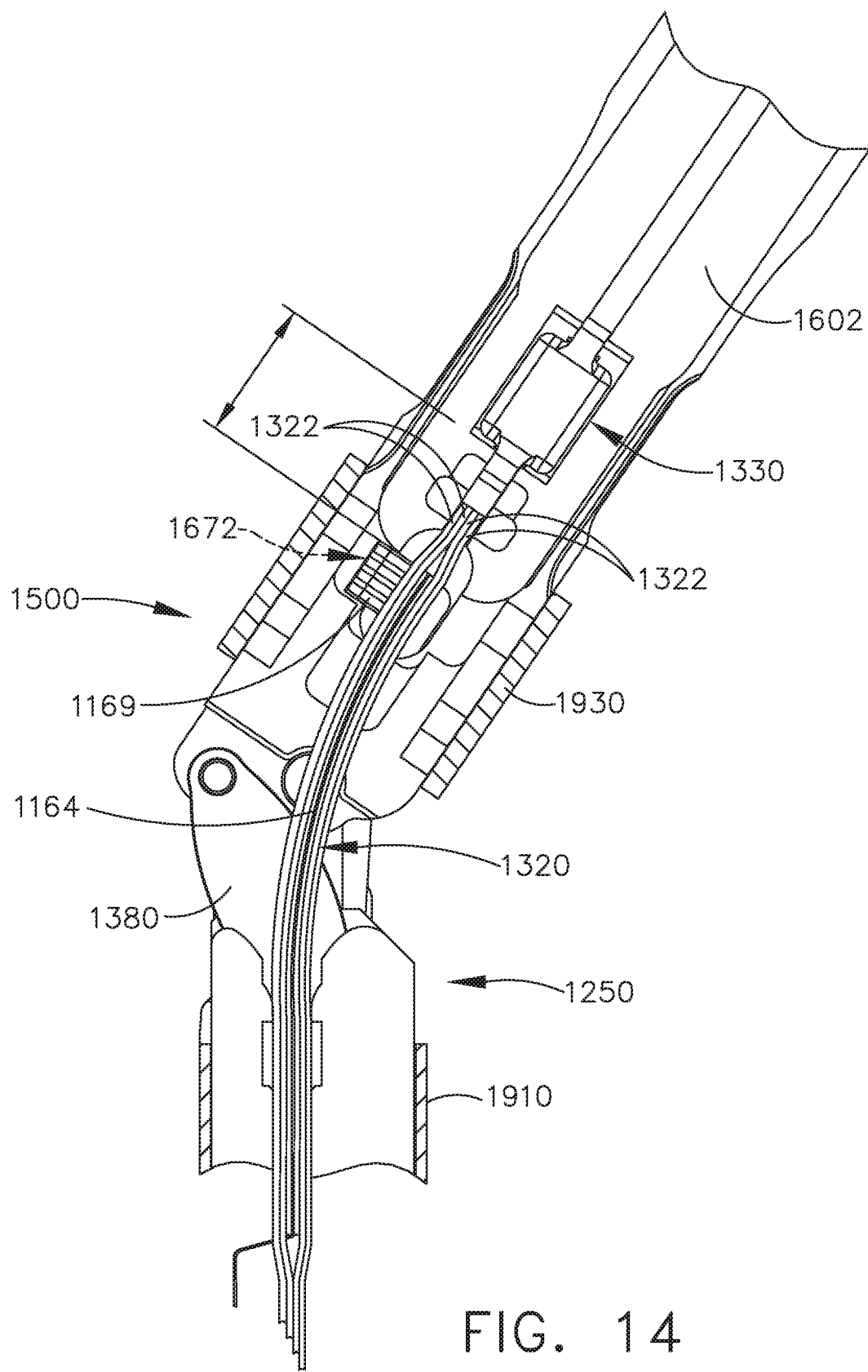
FIG. 14 is a top cross-sectional view of a portion of the interchangeable surgical tool assembly of FIGS. 1 and 5 with the end effector thereof in an articulated position according to one aspect of this disclosure.

In at least one arrangement, RF energy is supplied to the surgical tool assembly 1000 by a conventional RF generator 400 through a supply lead 402. In at least one arrangement, the supply lead 402 includes a male plug assembly 406 that is configured to be plugged into corresponding female connectors 410 that are attached to a segmented RF circuit 1160 on the an onboard circuit board 1152. See FIG. 15. Such arrangement facilitates rotational travel of the shaft and end effector 1500 about the shaft axis SA relative to the tool chassis 1210 by rotating the nozzle assembly 1240 without winding up the supply lead 402 from the generator 400. An onboard on/off power switch 420 is supported on the latch assembly 1280 and tool chassis 1210 for turning the RF generator on and off. When the tool assembly 1000 is operably coupled to the handle assembly 500 or robotic system, the onboard segmented RF circuit 1160 communicates with the microprocessor 560 through the connectors 1154 and 562. As shown in FIG. 1, the handle assembly 500 may also include a display screen 430 for viewing information about the progress of sealing, stapling, knife location, status of the cartridge, tissue, temperature, etc. As can also be seen FIG. 15, the slip ring assembly 1150 interfaces with a distal connector 1162 that includes a flexible shaft circuit strip or assembly 1164 that may include a plurality of narrow electrical conductors 1166 for stapling related activities and wider electrical conductors 1168 used for RF purposes. As shown in FIGS. 14 and 15, the flexible shaft circuit strip 1164 is centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue.

Turning again to FIG. 10, in at least one illustrated arrangement, the elongate channel 1602 includes a channel circuit 1670 supported in a recess 1621 that extends from the proximal end 1610 of the elongate channel 1602 to a distal location 1623 in the elongate channel bottom portion 1620. The channel circuit 1670 includes a proximal contact portion 1672 that contacts a distal contact portion 1169 of the flexible shaft circuit strip 1164 for electrical contact therewith. A distal end 1674 of the channel circuit 1670 is received within a corresponding wall recess 1625 formed in one of the channel walls 1622 and is folded over and attached to an upper edge 1627 of the channel wall 1622. A series of corresponding exposed contacts 1676 are provided in the distal end 1674 of the channel circuit 1670 As shown in FIG. 10. As can also be seen in FIG. 10, an end 1752 of a flexible cartridge circuit 1750 is attached to the distal micro-chip 1740 and is affixed to the distal end portion of the cartridge body 1710. Another end 1754 is folded over the edge of the cartridge deck surface 1711 and includes exposed contacts 1756 configured to make electrical contact with the exposed contacts 1676 of the channel circuit 1670. Thus, when the RF cartridge 1700 is installed in the elongate channel 1602, the electrodes as well as the distal micro-chip 1740 are powered and communicate with the onboard circuit board 1152 through contact between the flexible cartridge circuit 1750, the flexible channel circuit 1670, the flexible shaft circuit 1164 and the slip ring assembly 1150.

Figure 16A:
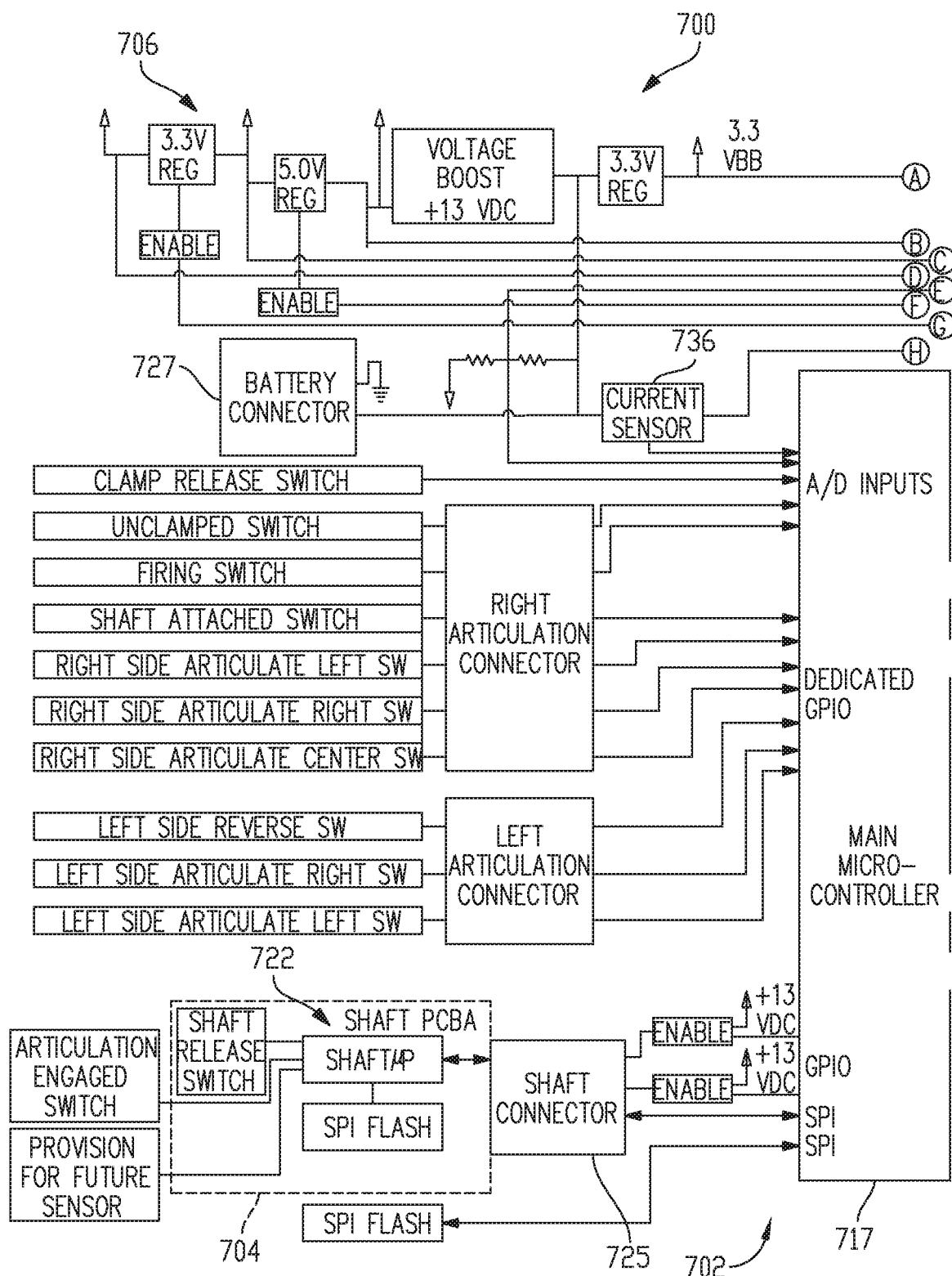
FIGS. 16A-16B is a block diagram of a control circuit of the surgical instrument of FIG. 1 spanning two drawing sheets according to one aspect of this disclosure.
Figure 16B:
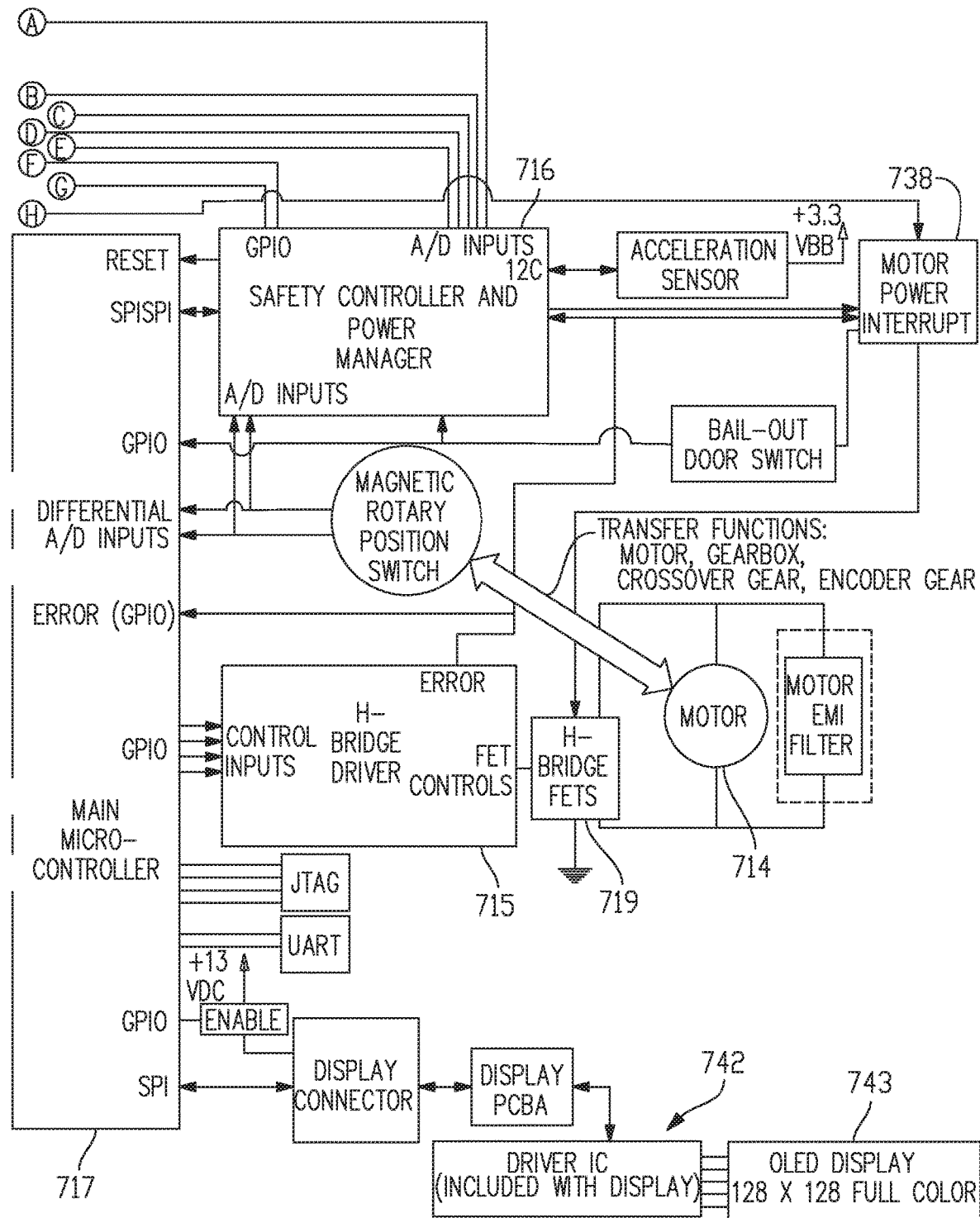

FIGS. 16A-16B is a block diagram of a control circuit 700 of the surgical instrument 10 of FIG. 1 spanning two drawing sheets according to one aspect of this disclosure. Referring primarily to FIGS. 16A-16B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 500 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-5) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 500 coupled to the surgical instrument 10 (FIGS. 1-5) and/or one or more controls for an end effector 1500 coupled to the interchangeable shaft assembly 500. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 500 and/or the shaft PCBA. The shaft PCBA may be coupled to the interchangeable shaft assembly 500 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 500 and/or end effectors 1500 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 500, and/or an end effector 1500 of the surgical instrument 10 (FIGS. 1-5). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-5). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-5), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 500 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-5) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include electrical conductorless switches, ultrasonic switches, accelerometers, inertial sensors, among others.

Figure 17:
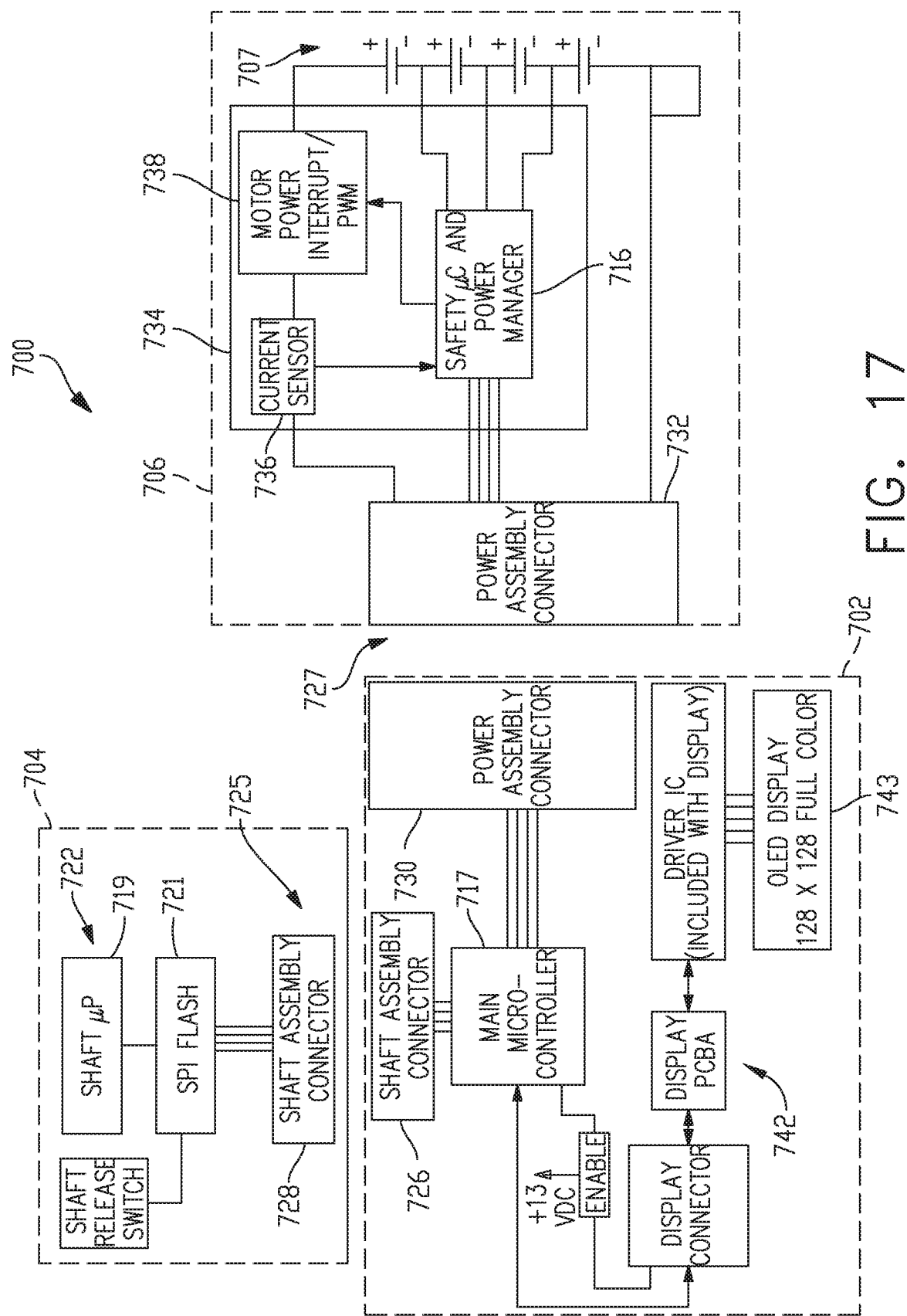
FIG. 17 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 17 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-5) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 16A-16B and 6) for controlling the operation of the surgical instrument 10 (FIGS. 1-5), the disclosure now turns to various configurations of the surgical instrument 10 (FIGS. 1-5) and control circuit 700.

Figure 18:
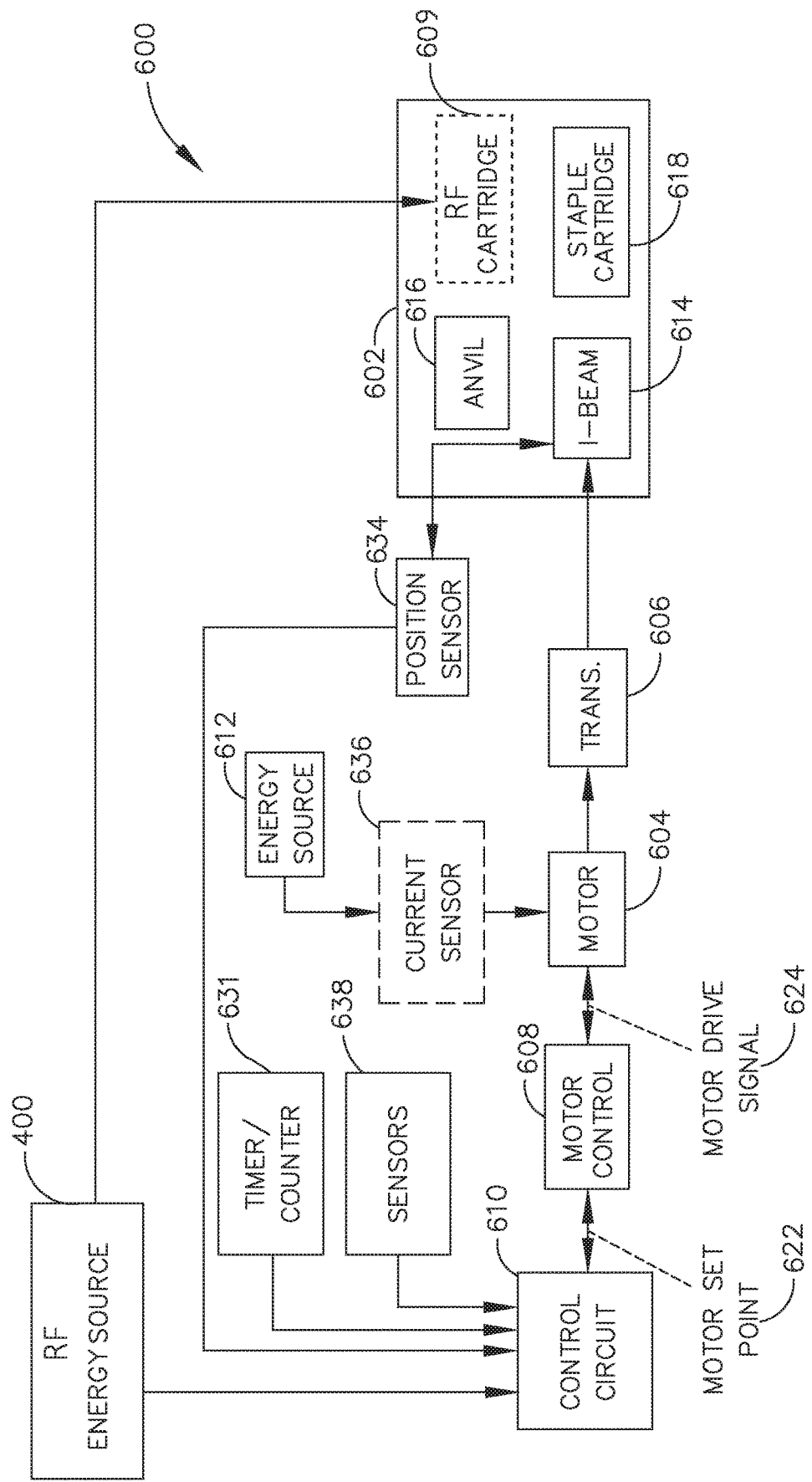
FIG. 18 is a schematic diagram of a surgical instrument configured to control various functions according to one aspect of this disclosure.

FIG. 18 is a schematic diagram of a surgical instrument 600 configured to control various functions according to one aspect of this disclosure. In one aspect, the surgical instrument 600 is programmed to control distal translation of a displacement member such as the I-beam 614. The surgical instrument 600 comprises an end effector 602 that may comprise an anvil 616, an I-beam 614, and a removable staple cartridge 618 which may be interchanged with an RF cartridge 609 (shown in dashed line). The end effector 602, anvil 616, I-beam 614, staple cartridge 618, and RF cartridge 609 may be configured as described herein, for example, with respect to FIGS. 1-15. For conciseness and clarity of disclosure, several aspects of the present disclosure may be described with reference to FIG. 18. It will be appreciated that the components shown schematically in FIG. 18 such as the control circuit 610, sensors 638, position sensor 634, end effector 602, I-beam 614, staple cartridge 618, RF cartridge 609, anvil 616, are described in connection with FIGS. 1-17 of this disclosure.

Accordingly, the components represented schematically in FIG. 18 may be readily substituted with the physical and functional equivalent components described in connection with FIGS. 1-17. For example, in one aspect, the control circuit 610 may be implemented as the control circuit 700 shown and described in connection with FIGS. 16-17. In one aspect, the sensors 638 may be implemented as a limit switch, electromechanical device, solid state switches, Hall-effect devices, magneto-resistive (MR) devices, giant magneto-resistive (GMR) devices, magnetometers, among others. In other implementations, the sensors 638 may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). In other implementations, the sensors 638 may include electrical conductorless switches, ultrasonic switches, accelerometers, inertial sensors, among others. In one aspect, the position sensor 634 may be implemented as an absolute positioning system comprising a magnetic rotary absolute positioning system implemented as an AS5055EQFT single-chip magnetic rotary position sensor available from Austria Microsystems, AG. The position sensor 634 may interface with the control circuit 700 to provide an absolute positioning system. The position may include multiple Hall-effect elements located above a magnet and coupled to a CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. In one aspect, the end effector 602 may be implemented as surgical end effector 1500 shown and described in connection with FIGS. 1, 2, and 4. In one aspect, the I-beam 614 may be implemented as the knife member 1330 comprising a knife body 1332 that operably supports a tissue cutting blade 1334 thereon and may further include anvil engagement tabs or features 1336 and channel engagement features or a foot 1338 as shown and described in connection with FIGS. 2-4, 8, 11 and 14. In one aspect, the staple cartridge 618 may be implemented as the standard (mechanical) surgical fastener cartridge 1400 shown and described in connection with FIG. 4. In one aspect, the RF cartridge 609 may be implemented as the radio frequency (RF) cartridge 1700 shown and described in connection with FIGS. 1, 2, 6, and 10-13. In one aspect, the anvil 616 may be implemented the anvil 1810 shown and described in connection with FIGS. 1, 2, 4, and 6. These and other sensors arrangements are described in commonly owned U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is incorporated herein by reference in its entirety.

The position, movement, displacement, and/or translation of a liner displacement member, such as the I-beam 614, can be measured by an absolute positioning system, sensor arrangement, and position sensor represented as position sensor 634. Because the I-beam 614 is coupled to the longitudinally movable drive member 540, the position of the I-beam 614 can be determined by measuring the position of the longitudinally movable drive member 540 employing the position sensor 634. Accordingly, in the following description, the position, displacement, and/or translation of the I-beam 614 can be achieved by the position sensor 634 as described herein. A control circuit 610, such as the control circuit 700 described in FIGS. 16A and 16B, may be programmed to control the translation of the displacement member, such as the I-beam 614, as described herein. The control circuit 610, in some examples, may comprise one or more microcontrollers, microprocessors, or other suitable processors for executing instructions that cause the processor or processors to control the displacement member, e.g., the I-beam 614, in the manner described. In one aspect, a timer/counter circuit 631 provides an output signal, such as elapsed time or a digital count, to the control circuit 610 to correlate the position of the I-beam 614 as determined by the position sensor 634 with the output of the timer/counter circuit 631 such that the control circuit 610 can determine the position of the I-beam 614 at a specific time (t) relative to a starting position. The timer/counter circuit 631 may be configured to measure elapsed time, count external evens, or time external events.

The control circuit 610 may generate a motor set point signal 622. The motor set point signal 622 may be provided to a motor controller 608. The motor controller 608 may comprise one or more circuits configured to provide a motor drive signal 624 to the motor 604 to drive the motor 604 as described herein. In some examples, the motor 604 may be a brushed DC electric motor, such as the motor 505 shown in FIG. 1. For example, the velocity of the motor 604 may be proportional to the motor drive signal 624. In some examples, the motor 604 may be a brushless direct current (DC) electric motor and the motor drive signal 624 may comprise a pulse-width-modulated (PWM) signal provided to one or more stator windings of the motor 604. Also, in some examples, the motor controller 608 may be omitted and the control circuit 610 may generate the motor drive signal 624 directly.

The motor 604 may receive power from an energy source 612. The energy source 612 may be or include a battery, a super capacitor, or any other suitable energy source 612. The motor 604 may be mechanically coupled to the I-beam 614 via a transmission 606. The transmission 606 may include one or more gears or other linkage components to couple the motor 604 to the I-beam 614. A position sensor 634 may sense a position of the I-beam 614. The position sensor 634 may be or include any type of sensor that is capable of generating position data that indicates a position of the I-beam 614. In some examples, the position sensor 634 may include an encoder configured to provide a series of pulses to the control circuit 610 as the I-beam 614 translates distally and proximally. The control circuit 610 may track the pulses to determine the position of the I-beam 614. Other suitable position sensor may be used, including, for example, a proximity sensor. Other types of position sensors may provide other signals indicating motion of the I-beam 614. Also, in some examples, the position sensor 634 may be omitted. Where the motor 604 is a stepper motor, the control circuit 610 may track the position of the I-beam 614 by aggregating the number and direction of steps that the motor 604 has been instructed to execute. The position sensor 634 may be located in the end effector 602 or at any other portion of the instrument.

The control circuit 610 may be in communication with one or more sensors 638. The sensors 638 may be positioned on the end effector 602 and adapted to operate with the surgical instrument 600 to measure the various derived parameters such as gap distance versus time, tissue compression versus time, and anvil strain versus time. The sensors 638 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 602. The sensors 638 may include one or more sensors.

The one or more sensors 638 may comprise a strain gauge, such as a micro-strain gauge, configured to measure the magnitude of the strain in the anvil 616 during a clamped condition. The strain gauge provides an electrical signal whose amplitude varies with the magnitude of the strain. The sensors 638 may comprise a pressure sensor configured to detect a pressure generated by the presence of compressed tissue between the anvil 616 and the staple cartridge 618. The sensors 638 may be configured to detect impedance of a tissue section located between the anvil 616 and the staple cartridge 618 that is indicative of the thickness and/or fullness of tissue located therebetween.

The sensors 638 may be is configured to measure forces exerted on the anvil 616 by the closure drive system. For example, one or more sensors 638 can be at an interaction point between the closure tube 1910 (FIGS. 1-4) and the anvil 616 to detect the closure forces applied by the closure tube 1910 to the anvil 616. The forces exerted on the anvil 616 can be representative of the tissue compression experienced by the tissue section captured between the anvil 616 and the staple cartridge 618. The one or more sensors 638 can be positioned at various interaction points along the closure drive system to detect the closure forces applied to the anvil 616 by the closure drive system. The one or more sensors 638 may be sampled in real time during a clamping operation by a processor as described in FIGS. 16A-16B. The control circuit 610 receives real-time sample measurements to provide analyze time based information and assess, in real time, closure forces applied to the anvil 616.

A current sensor 636 can be employed to measure the current drawn by the motor 604. The force required to advance the I-beam 614 corresponds to the current drawn by the motor 604. The force is converted to a digital signal and provided to the control circuit 610.

The RF energy source 400 is coupled to the end effector 602 and is applied to the RF cartridge 609 when the RF cartridge 609 is loaded in the end effector 602 in place of the staple cartridge 618. The control circuit 610 controls the delivery of the RF energy to the RF cartridge 609.

Typical electrical wires running between the handle assembly and an end effector may become tangled and potentially severed over time due to repeated bending of the articulating shaft. Therefore, the present disclosure provides a flexible circuit element that may withstand repeated shaft articulation and any other mechanical motions required to operate the end effector of the electrosurgical device.

As depicted in FIG. 14, the flexible shaft circuit strip 1164 may be disposed in part within the proximal closure tube 1910 and extend through the articulation connector 1920 into the surgical end effector 1500. Similarly, the knife bar 1320 may also be disposed in part within the proximal closure tube 1910 and extend through the articulation connector 1920 into the surgical end effector 1500. The flexible shaft circuit strip 1164 may be centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue. Together, the flexible shaft circuit strip 1164 and the laminated plates or bars 1322 that form the knife bar 1320 may comprise a flexible assembly to permit the knife bar 1320 to reciprocate while the articulation connector 1920 is bent.

Figure 19:
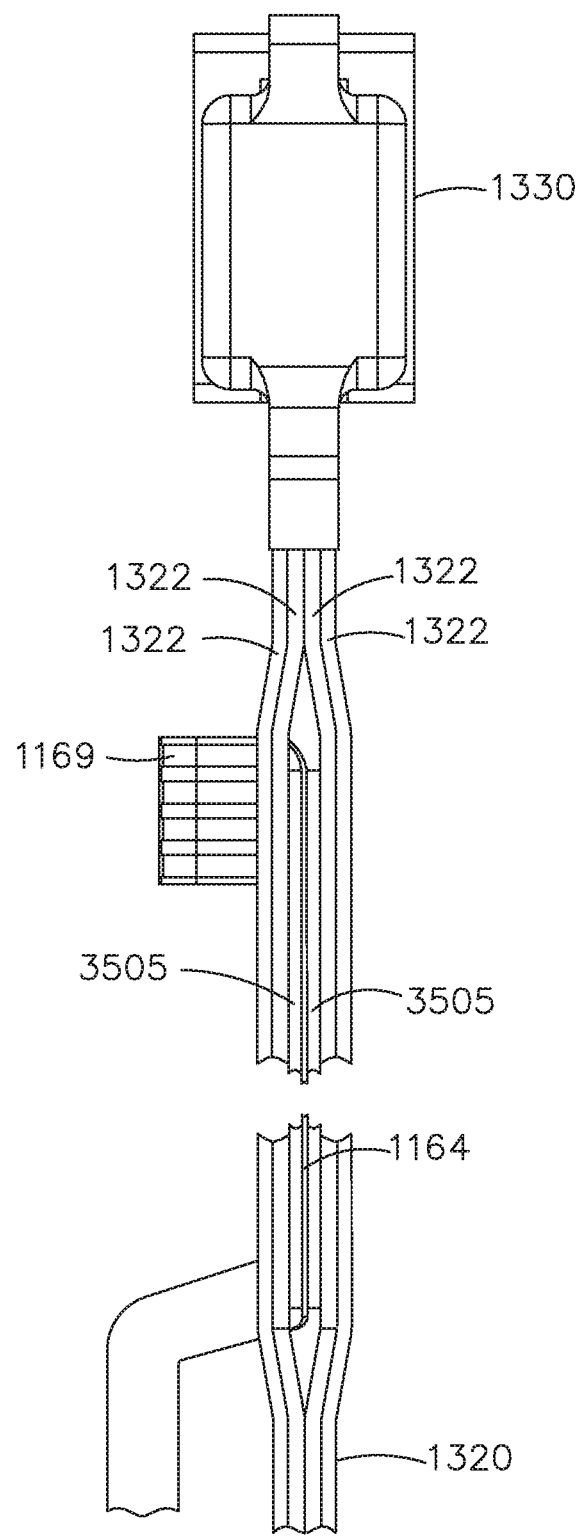
FIG. 19 is a top cross-section view of an aspect of a flexible assembly depicted in FIG. 14 according to one aspect of this disclosure.

FIG. 19 depicts in greater detail an aspect of a flexible assembly 3500. In the aspect of the flexible assembly 3500 depicted in FIG. 19, the knife bar 1320 is composed of two pairs of laminated plates 1322, in which one pair of laminated plates 1322 is disposed along a first side of the flexible shaft circuit strip 1164 and a second pair of laminated plates 1322 is disposed along a second side of the flexible shaft circuit strip 1164. Although the knife bar 1320 is disclosed as having two pairs of laminated plates 1322, it may be recognized that the knife bar 1320 may be composed of any even number of laminated plates 1322 in which a first half of the even number of laminated plates 1322 are disposed along a first side of the flexible shaft circuit strip 1164 and a second half of the even number of the laminated plates 1322 are disposed along a second side of the flexible shaft circuit strip 1164.

As depicted in FIG. 10, the flexible shaft circuit strip 1164 includes a distal contact portion 1169 that may be in electrical communication with a proximal contact portion 1672 of a channel circuit 1670 disposed within a wall recess 1625 formed in one of the channel walls 1622 of the elongate channel 1602. Thus, the distal end of the flexible shaft circuit strip 1164 may be in a fixed position relative to the elongate channel 1602 of the surgical end effector 1500. As depicted in FIG. 15, a proximal end of the flexible shaft circuit strip 1164 may be in electrical communication with a distal connector 1162 of a slip ring assembly 1150 disposed in the tool frame assembly 1200. Thus, the proximal end of the flexible shaft circuit strip 1164 may be in a fixed position relative to the tool frame assembly 1200. As depicted in FIG. 14, the flexible shaft circuit strip 1164 may thus traverse the articulation connector 1920 and may therefore bend on articulation of the articulation connector 1920.

The knife bar 1320 may similarly traverse the articulation connector 1920 from a proximal connection to the intermediate firing shaft portion 1310 disposed in the nozzle assembly 1240 to a distal connection at the knife member 1330, as depicted in FIG. 3. The knife bar 1320 may therefore be configured to reciprocate in order to activate the knife member 1330 while being flexible enough to bend when the articulation connector 1920 articulates.

It may be recognized that the reciprocating action of the knife bar 1320 along the sides of the flexible shaft circuit strip 1164 may cause rubbing and/or abrasion of any electrical traces or wires disposed on the flexible shaft circuit strip 1164. The electrical traces or wires may comprise wider wires/conductors for RF purposes and thinner wires for conventional stapling purposes (for example to conduct electrical control or sensing signals). Such wear may result in tears or gaps in the electrical wires that may compromise the ability of the electrical wires to conduct electrical, including RF, signals. Consequently, additional protection of the flexible shaft circuit strip 1164 may be required.

As depicted in FIG. 19, such protection may be provided by one or more leaf springs 3505 disposed on opposing sides of the flexible shaft circuit strip 1164. Each leaf spring 3505 may be disposed between a side of the flexible shaft circuit strip 1164 and an inner side of a laminated plate 1322. The leaf springs 3505 may remain fixed with respect to the flexible shaft circuit strip 1164, and may therefor protect each side of the flexible shaft circuit strip 1164 from wear from the knife bar 1320 during deployment of the knife member 1330. Each leaf spring 3505 may also provide physical support for the flexible shaft circuit strip 1164. Further, each leaf spring 3505 may provide a restoring force to the flexible shaft circuit strip 1164 to return the flexible shaft circuit strip 1164 to an essentially longitudinal (or unbent) geometry once the end effector 1500 is returned to a position co-axial with the shaft of the electrosurgical device. It may be recognized that in some aspect, the flexible assembly 3500 may also include one or more of such leaf springs 3505 in addition to the flexible shaft circuit strip 1164 and the plurality of laminated plates 1322.

Figure 20A:
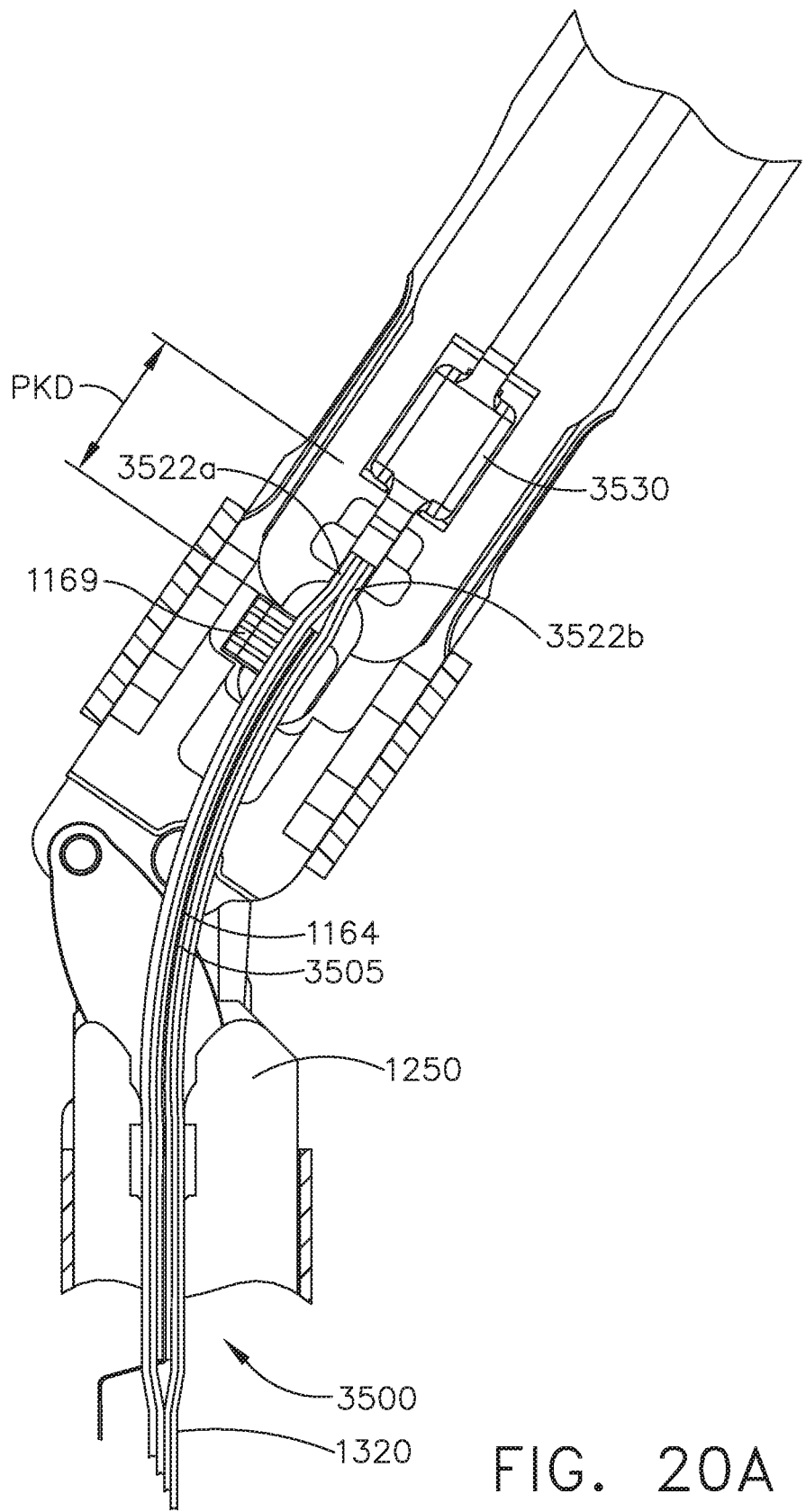
FIG. 20A is a top cross-section view of an aspect of the flexible assembly depicted in FIG. 14 for a knife member disposed at a proximal position as disposed within an aspect of an electrosurgical device according to one aspect of this disclosure.
Figure 20B:
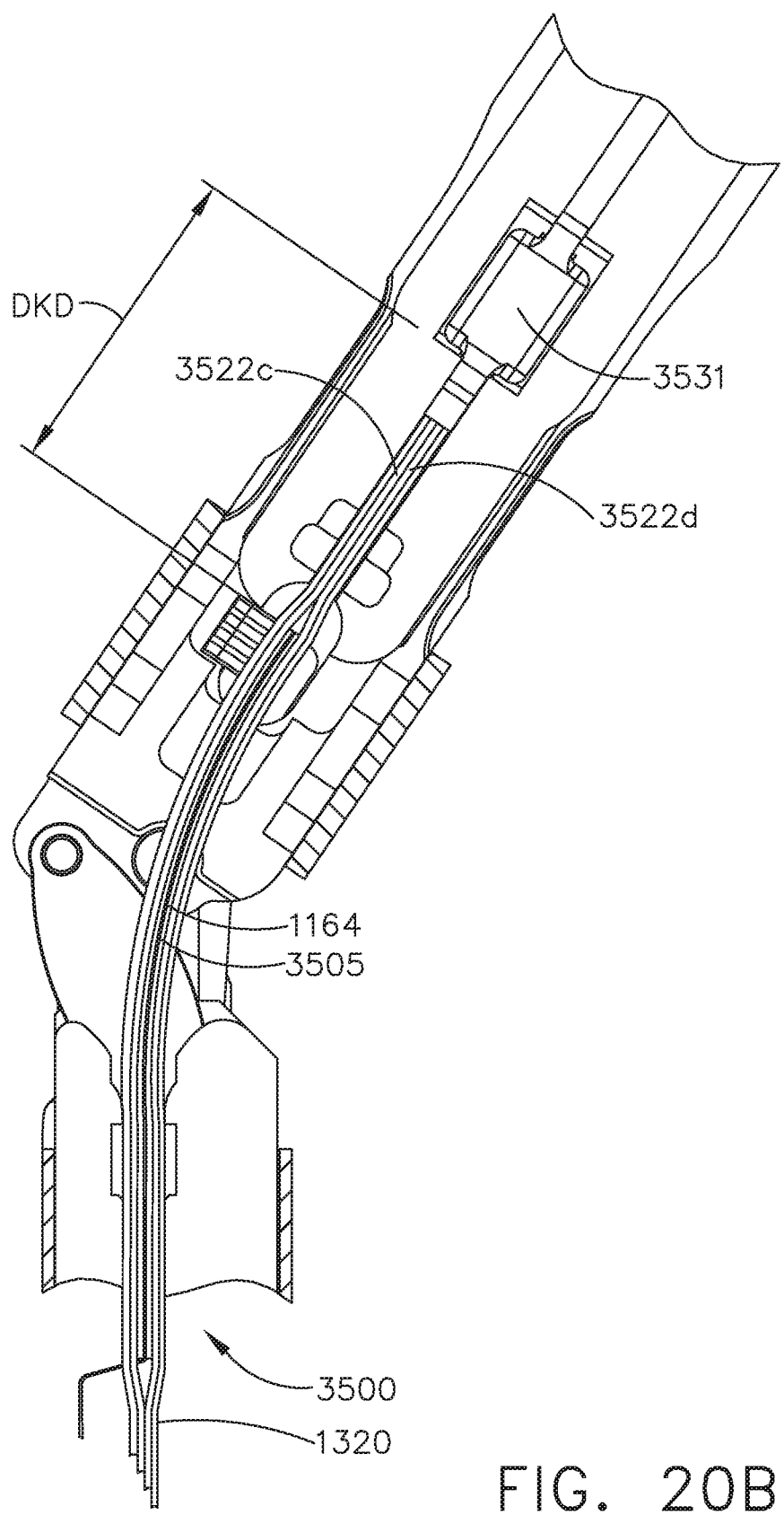
FIG. 20B is a top cross-section view of an aspect of the flexible assembly depicted in FIG. 14 for a knife member disposed at a distal position disposed within an aspect of an electrosurgical device according to one aspect of this disclosure.

FIG. 20A depicts the flexible assembly 3500 disposed within an electrosurgical device, in which the knife member 1330 is disposed at a proximal knife position 3530. FIG. 20B depicts the flexible assembly 3500 disposed within the electrosurgical device, in which the knife member 1330 is disposed at a distal knife position 3531. Although the articulation of the shaft of the electrosurgical device is depicted in a right direction (from the perspective of a use of the device) in FIGS. 20A and 20B, it should be recognized that the articulation of an electrosurgical device shaft may also be in a left direction (from the perspective of a use of the device), with the components of the flexible assembly 3500 suitably bent in the left direction.

FIG. 20A is similar to FIG. 14 and further points out additional details. For example, a proximal end of the flexible assembly 3500 may be stabilized within the spine assembly 1250 disposed within the proximal closure tube (1910, see FIG. 14). The distal end of the flexible assembly 2500 may be stabilized within the proximal end portion 1610 of the elongate channel (1602, see FIG. 4). The distal contact portion 1169 of the flexible shaft circuit strip 1164 may be both electrically and physically coupled to the proximal contact portion 1672 of the channel circuit (1670, see FIG. 10).

As depicted in FIG. 20A, the knife member may be located at a proximal knife position 3530. In one non-limiting aspect, the proximal knife position 3530 of the knife member may have a proximal knife distance (PKD), for example measured from a proximal end of the knife member to a distal end of the distal contact portion 1169 of the flexible shaft circuit strip 1164. FIG. 20B depicts the knife member located at a distal knife position 3531. In one non-limiting aspect, the distal knife position 3531 of the knife member may have a distal knife distance (DKD), for example measured from a proximal end of the knife member to a distal end of the distal contact portion 1169 of the flexible shaft circuit strip 1164. No limitation is implied regarding any explicit measurements of either the proximal knife distance PKD or the distal knife distance DKD. However, for the purpose of this disclosure, it may be accepted that the distal knife distance DKD is larger than the proximal knife distance PKD. It may be recognized during the use of the electrosurgical system that the knife member 1330 may traverse from the proximal knife position 3530 to the distal knife position 3531 or from the distal knife position 3531 to the proximal knife position 3530.

As disclosed above, the distal end of the flexible shaft circuit strip 1164 may be in a fixed position relative to the surgical end effector 1500 and the proximal end of the flexible shaft circuit strip 1164 may be in a fixed position relative to the tool frame assembly 1200. Additionally, the leaf springs 3505 may remain in a fixed position with respect to the flexible shaft circuit strip 1164. In one non-limiting aspect, a first leaf spring 3505 may be disposed proximate to or against a first side of the flexible shaft circuit strip 1164, and a second leaf spring 3505 may be disposed proximate to or against a second or opposing side of the flexible shaft circuit strip 1164. As the knife bar 1320 moves the knife member 1330 to either the distal knife position 3531 or the proximal knife position 3530, the laminated plates 1322 of the knife bar 1320 move in a sliding manner in a longitudinal direction with respect to the fixed position of the flexible shaft circuit strip 1164 and the leaf springs 3505.

While the knife bar 1320 is in a proximal aspect and the knife member 1330 is at the proximal knife position 3530, a portion of the first pair of laminated plates 1322 may be located at a first proximal position 3522a along an outer side of a first leaf spring 3505 and a portion of the second pair of laminated plates 1322 may be located at a second proximal position 3522b along an outer side of a second leaf spring 3505. In this configuration, at portion of the flexible shaft circuit strip 1164 and a portion of the leaf springs 3505 separate those portions of the laminated plates 1322 located at the first proximal position 3522a and the second proximal position 3522b. When the knife bar 1320 is moved distally so that the knife member 1330 is at the distal knife position 3531, the portion of the first pair of laminated plates 1322 located at the first proximal position 3522a may traverse in the distal direction to a first distal position 3522c. Similarly, when the knife bar 1320 is moved distally so that the knife member 1330 is at the distal knife position 3531, the portion of the second pair of laminated plates 1322 located at the second proximal position 3522b may traverse in the distal direction to a second distal position 3522d. In this manner at least some portion of the laminated plates 1322 move in a sliding manner with respect to the leaf springs 3505.

As a result of the motion of the knife bar 1320 in the distal direction, the portion of the first pair of laminated plates in the first distal position 3522c and the portion of the second pair of laminated plates in the second distal position 3522d are no longer separated by the flexible shaft circuit strip 1164 and the leaf springs 3505. Thus, an inner surface of the portion of the first pair of laminated plates in the first distal position 3522c may contact an inner surface of the portion of the second pair of laminated plates in the second distal position 3522d when the knife bar 1320 is moved in the distal direction.

It may similarly be understood that when the knife bar 1320 is moved in a proximal direction, thereby moving the knife member 1330 from the distal knife position 3531 to the proximal knife position 3530, the portion of the first pair of laminated plates 1322 located at the first distal position 3522c may traverse in the proximal direction to the first proximal position 3522a. Similarly, when the knife bar 1320 is moved in a proximal direction, the portion of the second pair of laminated plates 1322 located at the second distal position 3522d may traverse in the proximal direction to the second proximal position 3522b. As a result of the motion of the knife bar 1320 in the proximal direction, the portion of the first pair of laminated plates in the first proximal position 3522*a* and the portion of the second pair of laminated plates in the second proximal position 3522*b* may be separated by the leaf springs 3505 and the flexible shaft circuit strip 1164.

Figures 21A, 21B:
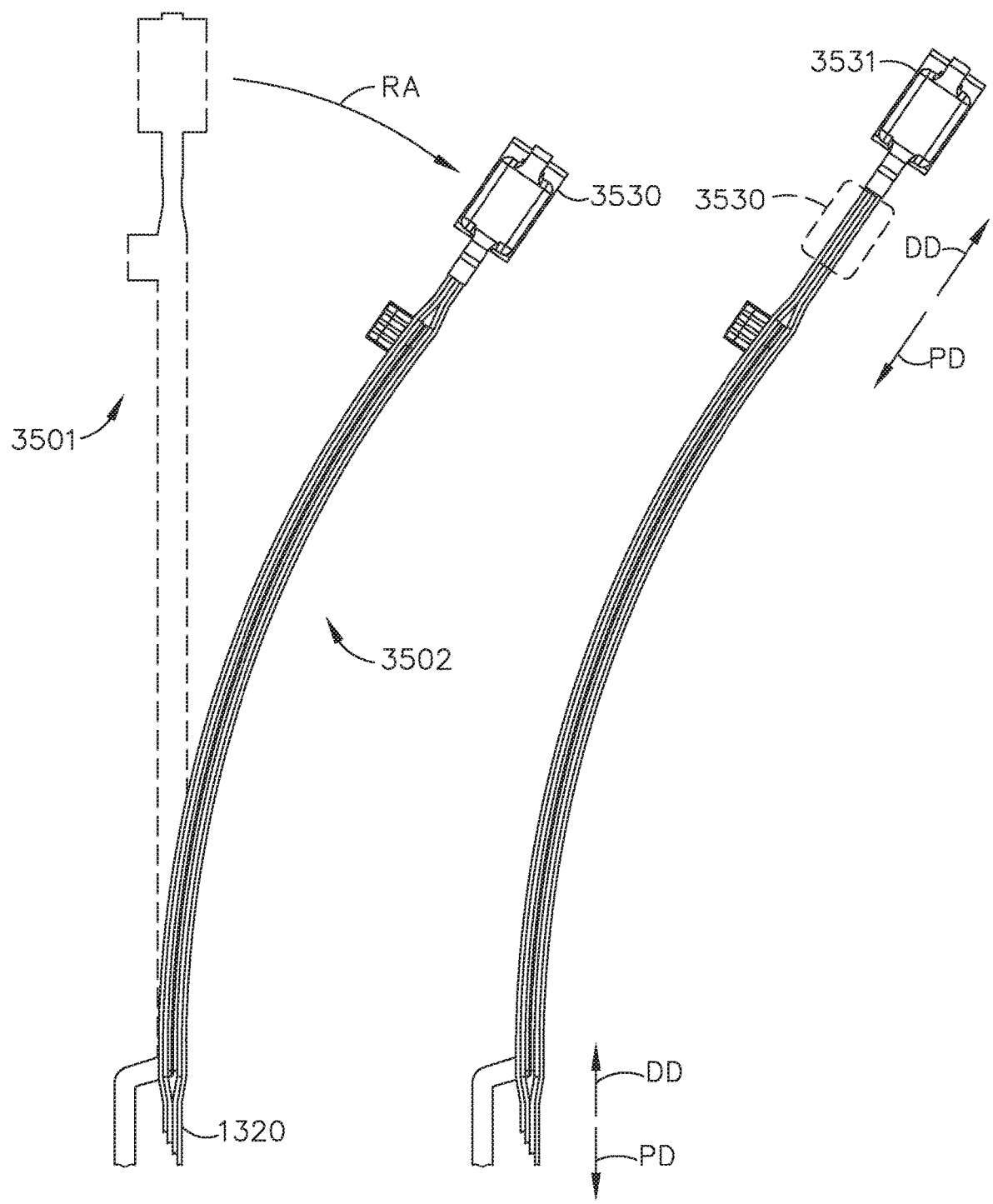
FIG. 21A is a top cross-section view of an aspect of the flexible assembly depicted in FIG. 14 for a knife member disposed at a proximal position according to one aspect of this disclosure.
FIG. 21B is a top cross-section view of an aspect of the flexible assembly depicted in FIG. 14 for a knife member disposed at a distal position according to one aspect of this disclosure.

FIGS. 21A and 21B depict the flexible assembly 3500 of FIGS. 20A and 20B independent of structures that may house the flexible assembly 3500 in an electrosurgical device. In particular, FIG. 21A depicts an unarticulated flexible assembly 3501 (dotted line) and an articulated flexible assembly 3502 after a right articulation RA. FIG. 21B depicts the effect of a motion of the knife bar 1320 in a distal direction DD, thereby moving the knife member 1330 from the proximal knife position 3530 to the distal knife position 3531. FIG. 21B additionally depicts the effect of a motion of the knife bar 1320 in a proximal direction PD thereby moving the knife member 1330 from the distal knife position 3531 to the proximal knife position 3530.

As disclosed above with respect to FIGS. 16 and 20A, B, a flexible assembly 3500 may include a flexible shaft circuit strip 1164 disposed between a pair of leaf springs 3505, and a knife bar 1320 comprising two pairs of laminated plates 1322, in which a pair of laminated plates 1322 is disposed along an outer surface of each of the leaf springs 3505. Such leaf springs 3505 may provide protection of the surfaces of the flexible shaft circuit strip 1164 against abrasion and wear caused by the reciprocating motion of the laminated plates 1322. In an alternative aspect, the flexible assembly 3500 may lack the pair of leaf springs 3505 and the laminated plates 1322 may be disposed directly against the sides of the flexible shaft circuit strip 1164. The motion of the laminated plates 1322 against the sides of the flexible shaft circuit strip 1164 may include such motions as disclosed above in detail with respect to FIGS. 20A, B. Such an alternative aspect of a flexible assembly 3500 lacking the leaf springs 3505 may find use for a flexible assembly 3500 in which the flexible shaft circuit strip 1164 includes a protective coating on its sides, thereby obviating the need for protective leaf springs 3505.

It may be further recognized that the flexible assembly 3500 disclosed above may find utility in an electrosurgical device that includes an end effector configured to include a surgical staple/fastener cartridge, a radio frequency (RF) cartridge, or to releasably accept either a surgical staple/fastener cartridge or a radio frequency (RF) cartridge.

Disclosed above are aspects of a flexible assembly configured for use within an electrosurgical system comprising an articulating shaft. The flexible assembly may span an articulation connector and include a flexible shaft circuit strip configured to bend in accordance with the bending of the articulation connector. The flexible shaft circuit strip may be configured to permit communication of electrical signals from a handle assembly at a proximal end of the articulating shaft to an end effector at a distal end of the articulating shaft. The flexible assembly may also include one or more components configured to move in a transverse manner along a longitudinal axis of the articulating shaft to control one or more operations of the end effector. The flexible assembly may further include additional components configured to support or protect the flexible shaft circuit strip and/or the components configured to move in a transverse manner along the longitudinal axis of the articulating shaft.

Although a flexible assembly is described with respect to a motor driven surgical system as depicted in FIGS. 1-15 and as disclosed above, it may be recognized that a flexible assembly may not be limited to a surgical system having the specific components or functions of such a motor driven surgical system. Such a flexible assembly may be incorporated into any surgical system comprising at least an articulating shaft having a body or handle assembly at a proximal end of the articulating shaft and an end effector at a distal end of the articulating shaft.

Thus, a flexible shaft circuit strip of a flexible assembly may be configured to conduct any one or more electrical signals including DC electrical signals, AC electrical signals, digital electrical signals, analog electrical signals, RF electrical signals, or any combination or combinations of such electrical signals. The flexible shaft circuit strip may comprise any flexible non-conducting material on which or in which are disposed any number, type, or size of conducting wires or traces. The flexible shaft circuit strip may comprise any number of layers. The flexible shaft circuit strip may further comprise any one or more electronic components such as discrete circuits (for example, resistors, capacitors, and inductors) or integrated circuits. The flexible shat circuit strip may further include protective layers to cover over the one or more conducting wires or traces, and or electronic components. The flexible assembly may include one or more springs, such as leaf springs, disposed on one or more sides of the flexible shaft circuit strip to provide a restoring force after the surgical system is returned from an articulated position. Alternatively, the flexible shaft circuit strip may incorporate such leaf springs in the body of the flexible shaft circuit strip.

The components configured to move in a transverse manner along the longitudinal axis of the articulating shaft may include any number or type of component or components capable of both a transverse motion and a flexible bending motion. Non-limiting examples of such components may include wires, bands, plates, and flexible shafts. One or more of such components configured to move in a transverse manner may be included in the flexible assembly. Multiple components may move in a concerted manner or may move independently. Multiple components may be disposed along a single side of the flexible shaft circuit strip. Alternatively, some number of the multiple components may be disposed along a first side of the flexible shaft circuit strip while a different number of the multiple components may be disposed along a second side of the flexible shaft circuit strip. The components configured to move in a transverse manner may be operatively coupled to any movable components either in a proximal end or a distal end of the articulating shaft, without limitation regarding the functions of such movable components.

The flexible assembly may also include any number or type of components configured to protect or support the flexible shaft circuit strip and/or the components configured to move in a transverse manner. For example, additional components may include any number or type of component configured to protect one or more surfaces of the flexible shaft circuit strip including, for example, protective sheets or sheaths. The additional components may include a frame to support the flexible shaft circuit strip. The additional components may further include protective enclosures for the components configured to move in a transverse manner such as cannulae.

Aspects of the surgical instrument may be practiced without the specific details disclosed herein. Some aspects have been shown as block diagrams rather than detail. Parts of this disclosure may be presented in terms of instructions that operate on data stored in a computer memory. Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program, which at least partially carries out processes and/or devices described herein), electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components, logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a electrical conductor communications link, a electrical conductorless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Various aspects of the subject matter described herein are set out in the following numbered examples:

Example 1

A motor driven surgical system comprising: a handle assembly; and an interchangeable surgical tool assembly, operatively coupled to the handle assembly, comprising: a nozzle assembly; a proximal closure tube having a proximal end operatively coupled to a distal end of the nozzle assembly; an articulation connector having a proximal end operatively coupled to a distal end of the proximal closure tube; a surgical end effector comprising a first jaw and a second jaw and having a proximal end operatively coupled to a distal end of the articulation connector; a flexible shaft circuit strip disposed within at least a portion of the proximal closure tube, at least a portion of the articulation connector, and at least a portion of the surgical end effector; a knife member slideably disposed within the surgical end effector; and a knife bar operatively connected to a proximal end of the knife member, wherein the knife bar comprises a first laminated plate disposed on a first side of the flexible shaft circuit strip and a second laminated plate disposed on a second side of the flexible shaft circuit strip, and wherein the knife bar is configured to reciprocate along a longitudinal axis of the proximal closure tube.

Example 2

The motor driven surgical system of Example 1, wherein the first laminated plate comprises a first pair of laminated plates and the second laminated plate comprises a second pair of laminated plates.

Example 3

The motor driven surgical system of one or more of Example 1 through Example 2, wherein the first laminated plate is configured to reciprocate along the first side of the flexible shaft circuit strip and the second laminated plate is configured to reciprocate along the second side of the flexible shaft circuit strip.

Example 4

The motor driven surgical system of one or more of Example 1 through Example 3, further comprising a first leaf spring disposed between the first side of the flexible shaft circuit strip and the first laminated plate, and a second leaf spring disposed between the second side of the flexible shaft circuit strip and the second laminated plate.

Example 5

The motor driven surgical system of Example 4, wherein the first laminated plate is configured to reciprocate along a first side of the first leaf spring and the second laminated plate is configured to reciprocate along a first side of the second leaf spring.

Example 6

The motor driven surgical system of one or more of Example 4 through Example 5, wherein the first leaf spring and the second leaf spring are disposed within at least a portion of the articulation connector and at least a portion of the surgical end effector.

Example 7

The motor driven surgical system of one or more of Example 4 through Example 6, wherein the first leaf spring and the second leaf spring are configured to bend around an articulation axis transverse to a longitudinal axis of the proximal closure tube.

Example 8

The motor driven surgical system of one or more of Example 1 through Example 7, further comprising an elongated channel disposed within the first jaw, wherein the elongated channel is configured to releasably receive a surgical fastener cartridge.

Example 9

The motor driven surgical system of one or more of Example 1 through Example 8, further comprising an elongated channel disposed within the first jaw, wherein the elongated channel is configured to releasably receive a radiofrequency cartridge.

Example 10

The motor driven surgical system of Example 9, further comprising a channel circuit disposed along an inner longitudinal side of the elongated channel, wherein the channel circuit comprises a proximal contract portion configured to electrically couple to a distal contact portion of the flexible shaft circuit strip, and wherein the channel circuit comprises a distal contract portion configured to electrically couple to a flexible cartridge circuit disposed on a surface of the radiofrequency cartridge.

Example 11

A flexible assembly for use within an articulated component of a motor driven surgical system, the flexible assembly comprising: a flexible shaft circuit strip; and a knife bar comprising a first laminated plate disposed along a first side of the flexible shaft circuit strip and a second laminated plate disposed along a second side of the flexible shaft circuit strip, wherein the knife bar is configured to reciprocate along a longitudinal axis of the flexible shaft circuit strip.

Example 12

The flexible assembly of Example 11, wherein the flexible assembly is configured to bend around an articulation axis transverse to a longitudinal axis of the flexible shaft circuit strip.

Example 13

The flexible assembly of one or more of Example 11 through Example 12, wherein the first laminated plate comprises a first pair of laminated plates and the second laminated plate comprises a second pair of laminated plates.

Example 14

The flexible assembly of one or more of Example 11 through Example 13, wherein a side of a first portion of the first laminated plate is disposed along the first side of the flexible shaft circuit strip and a side of a first portion of the second laminated plate is disposed along the second side of the flexible shaft circuit strip when the flexible assembly is in a first state, and wherein the side of the first portion of the first laminated plate is disposed along the side of the first portion of the second laminated plate when the flexible assembly is in a second state.

Example 15

The flexible assembly of one or more of Example 11 through Example 14, further comprising a first leaf spring disposed between the first side of the flexible shaft circuit strip and the first laminated plate, and a second leaf spring disposed between the second side of the flexible shaft circuit strip and the second laminated plate.

Example 16

The flexible assembly of Example 15, wherein the first laminated plate is configured to reciprocate along a first side of the first leaf spring and the second laminated plate is configured to reciprocate along a first side of the second leaf spring.

Example 17

The flexible assembly of one or more of Example 15 through Example 16, wherein a side of a first portion of the first laminated plate is disposed along a first side of the first leaf spring and a side of a first portion of the second laminated plate is disposed along a first side of the second leaf spring when the flexible assembly is in a first state, and wherein the side of the first portion of the first laminated plate is disposed along the side of the first portion of the second laminated plate when the flexible assembly is in a second state.

Example 18

The flexible assembly of one or more of Example 11 through Example 17, wherein the flexible shaft circuit strip comprises a distal contact portion.

Example 19

The flexible assembly of one or more of Example 11 through Example 18, wherein the flexible shaft circuit strip comprises a plurality of narrow wires and a plurality of wider wires.

Example 20

The flexible assembly of Example 19, wherein the plurality of wider wires is configured to conduct a radiofrequency signal.

The invention claimed is:
1. A motor driven surgical system comprising:
a handle assembly; and
an interchangeable surgical tool assembly, operatively coupled to the handle assembly, comprising:
a nozzle assembly;
a proximal closure tube having a proximal end operatively coupled to a distal end of the nozzle assembly;
an articulation connector having a proximal end operatively coupled to a distal end of the proximal closure tube;

a surgical end effector comprising a first jaw and a second jaw and having a proximal end operatively coupled to a distal end of the articulation connector;

a flexible shaft circuit strip disposed within at least a portion of the proximal closure tube, at least a portion of the articulation connector, and at least a portion of the surgical end effector;

a knife member slideably disposed within the surgical end effector; and a knife bar operatively connected to a proximal end of the knife member, wherein the knife bar comprises a first laminated plate disposed on a first side of the flexible shaft circuit strip and a second laminated plate disposed on a second side of the flexible shaft circuit strip, wherein the knife bar further comprising a first leaf spring disposed between the first side of the flexible shaft circuit strip and the first laminated plate, and a second leaf spring disposed between the second side of the flexible shaft circuit strip and the second laminated plate, and wherein the knife bar is configured to reciprocate along a longitudinal axis of the proximal closure tube.

2. The motor driven surgical system of claim 1, wherein the knife bar further comprises a third laminated plate disposed on the first side of the flexible shaft circuit strip and a fourth laminated plate disposed on the second side of the flexible shaft circuit strip.

3. The motor driven surgical system of claim 1, wherein the first laminated plate is configured to reciprocate along the first side of the flexible shaft circuit strip and the second laminated plate is configured to reciprocate along the second side of the flexible shaft circuit strip.

4. The motor driven surgical system of claim 1, wherein the first laminated plate is configured to reciprocate along a first side of the first leaf spring and the second laminated plate is configured to reciprocate along a first side of the second leaf spring.

5. The motor driven surgical system of claim 1, wherein the first leaf spring and the second leaf spring are disposed within at least a portion of the articulation connector and at least a portion of the surgical end effector.

6. The motor driven surgical system of claim 1, wherein the first leaf spring and the second leaf spring are configured to bend around an articulation axis transverse to a longitudinal axis of the proximal closure tube.

7. The motor driven surgical system of claim 1, further comprising an elongated channel disposed within the first jaw, wherein the elongated channel is configured to releasably receive a surgical fastener cartridge.

8. The motor driven surgical system of claim 1, further comprising an elongated channel disposed within the first jaw, wherein the elongated channel is configured to releasably receive a radiofrequency cartridge.

9. A motor driven surgical system comprising:
a handle assembly; and
an interchangeable surgical tool assembly, operatively coupled to the handle assembly, comprising:
a nozzle assembly;
a proximal closure tube having a proximal end operatively coupled to a distal end of the nozzle assembly;
an articulation connector having a proximal end operatively coupled to a distal end of the proximal closure tube;
a surgical end effector comprising a first jaw and a second jaw and having a proximal end operatively coupled to a distal end of the articulation connector;

an elongated channel disposed within the first jaw, wherein the elongated channel is configured to releasably receive a radiofrequency cartridge;

a flexible shaft circuit strip disposed within at least a portion of the proximal closure tube, at least a portion of the articulation connector, and at least a portion of the surgical end effector;

a knife member slideably disposed within the surgical end effector; and a knife bar operatively connected to a proximal end of the knife member, wherein the knife bar comprises a first laminated plate disposed on a first side of the flexible shaft circuit strip and a second laminated plate disposed on a second side of the flexible shaft circuit strip, wherein the knife bar is configured to reciprocate along a longitudinal axis of the proximal closure tube;

wherein the motor driven surgical system further comprises a channel circuit disposed along an inner longitudinal side of the elongated channel, wherein the channel circuit comprises a proximal contract portion configured to electrically couple to a distal contact portion of the flexible shaft circuit strip, and wherein the channel circuit comprises a distal contract portion configured to electrically couple to a flexible cartridge circuit disposed on a surface of the radiofrequency cartridge.

10. A motor driven surgical system comprising:
a surgical tool assembly, comprising:
a proximal closure tube;
an articulation connector having a proximal end operatively coupled to a distal end of the proximal closure tube;
a surgical end effector comprising a first jaw and a second jaw and having a proximal end operatively coupled to a distal end of the articulation connector;
a flexible shaft circuit strip disposed within at least a portion of the proximal closure tube, at least a portion of the articulation connector, and at least a portion of the surgical end effector;
a knife member slideably disposed within the surgical end effector; and
a knife bar operatively connected to a proximal end of the knife member,
wherein the knife bar comprises a first laminated plate disposed on a first side of the flexible shaft circuit strip and a second laminated plate disposed on a second side of the flexible shaft circuit strip,
wherein the knife bar further comprising a first leaf spring disposed between the first side of the flexible shaft circuit strip and the first laminated plate, and a second leaf spring disposed between the second side of the flexible shaft circuit strip and the second laminated plate, and
wherein the knife bar is configured to reciprocate along a longitudinal axis of the proximal closure tube.

11. The motor driven surgical system of claim 10, wherein the knife bar further comprises a third laminated plate disposed on the first side of the flexible shaft circuit strip and a fourth laminated plate disposed on the second side of the flexible shaft circuit strip.

12. The motor driven surgical system of claim 10, wherein the first laminated plate is configured to reciprocate along the first side of the flexible shaft circuit strip and the second laminated plate is configured to reciprocate along the second side of the flexible shaft circuit strip.

13. The motor driven surgical system of claim 10, wherein the first laminated plate is configured to reciprocate along a first side of the first leaf spring and the second laminated plate is configured to reciprocate along a first side of the second leaf spring.

14. The motor driven surgical system of claim 10, wherein the first leaf spring and the second leaf spring are disposed within at least a portion of the articulation connector and at least a portion of the surgical end effector.

15. The motor driven surgical system of claim 10, wherein the first leaf spring and the second leaf spring are configured to bend around an articulation axis transverse to the longitudinal axis of the proximal closure tube.

16. The motor driven surgical system of claim 10, further comprising an elongated channel disposed within the first jaw, wherein the elongated channel is configured to releasably receive a surgical fastener cartridge.

17. The motor driven surgical system of claim 10, further comprising an elongated channel disposed within the first jaw, wherein the elongated channel is configured to releasably receive a radiofrequency cartridge.

18. A motor driven surgical system comprising:
a surgical tool assembly, comprising:
    a proximal closure tube;
    an articulation connector having a proximal end operatively coupled to a distal end of the proximal closure tube;
    a surgical end effector comprising a first jaw and a second jaw and having a proximal end operatively coupled to a distal end of the articulation connector;
    an elongated channel disposed within the first jaw, wherein the elongated channel is configured to releasably receive a radiofrequency cartridge;
    a flexible shaft circuit strip disposed within at least a portion of the proximal closure tube, at least a portion of the articulation connector, and at least a portion of the surgical end effector;
    a knife member slideably disposed within the surgical end effector; and
    a knife bar operatively connected to a proximal end of the knife member,
wherein the knife bar comprises a first laminated plate disposed on a first side of the flexible shaft circuit strip and a second laminated plate disposed on a second side of the flexible shaft circuit strip,
wherein the knife bar is configured to reciprocate along a longitudinal axis of the proximal closure tube,
wherein the motor drive surgical system further comprises a channel circuit disposed along an inner longitudinal side of the elongated channel,
wherein the channel circuit comprises a proximal contract portion configured to electrically couple to a distal contact portion of the flexible shaft circuit strip, and
wherein the channel circuit comprises a distal contract portion configured to electrically couple to a flexible cartridge circuit disposed on a surface of the radiofrequency cartridge.

19. A motor driven surgical system comprising:
a surgical tool assembly, comprising:
    a proximal closure tube;
    an articulation connector having a proximal end operatively coupled to a distal end of the proximal closure tube;
    a surgical end effector comprising a first jaw and a second jaw and having a proximal end operatively coupled to a distal end of the articulation connector;
    a flexible shaft circuit strip disposed within at least a portion of the proximal closure tube, at least a portion of the articulation connector, and at least a portion of the surgical end effector;
    a knife member slideably disposed within the surgical end effector; and
    a knife bar operatively connected to a proximal end of the knife member,
wherein the knife bar comprises a laminated plate disposed on a side of the flexible shaft circuit strip, and a leaf spring disposed between the side of the flexible shaft circuit strip and the laminated plate, and
wherein the knife bar is configured to reciprocate along a longitudinal axis of the proximal closure tube.

* * * * *